United States Patent
Kaplan et al.

(10) Patent No.: US 8,906,393 B2
(45) Date of Patent: Dec. 9, 2014

(54) BIOFILM INHIBITING COMPOSITION

(75) Inventors: Jeffrey B. Kaplan, Monsey, NY (US); Nataliya V. Balashova, Hamilton, NJ (US); Scott C. Kachlany, Bridgewater, NJ (US); Evguenii Vinogradov, Ottawa (CA)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/359,277

(22) Filed: Jan. 26, 2012

(65) Prior Publication Data

US 2012/0225098 A1 Sep. 6, 2012

Related U.S. Application Data

(60) Provisional application No. 61/436,411, filed on Jan. 26, 2011.

(51) Int. Cl.

| | | |
|---|---|---|
| *A61K 9/00* | (2006.01) | |
| *C12N 9/10* | (2006.01) | |
| *C12P 19/04* | (2006.01) | |
| *C12N 15/52* | (2006.01) | |
| *C08B 37/00* | (2006.01) | |
| *A61K 45/06* | (2006.01) | |
| *A61L 31/16* | (2006.01) | |
| *A61L 31/10* | (2006.01) | |
| *A61L 27/54* | (2006.01) | |
| *A61K 31/715* | (2006.01) | |
| *A61L 27/34* | (2006.01) | |
| *A01N 43/16* | (2006.01) | |
| *A61L 29/16* | (2006.01) | |
| *C12N 9/90* | (2006.01) | |
| *A61L 29/08* | (2006.01) | |
| *C08L 5/00* | (2006.01) | |
| *A01N 63/02* | (2006.01) | |

(52) U.S. Cl.
CPC .............. *C12N 15/52* (2013.01); *C12N 9/1048* (2013.01); *C12P 19/04* (2013.01); *C08B 37/0036* (2013.01); *A61K 45/06* (2013.01); *A61L 31/16* (2013.01); *C08B 37/0003* (2013.01); *A61L 31/10* (2013.01); *A61L 27/54* (2013.01); *A61K 31/715* (2013.01); *A61L 27/34* (2013.01); *A01N 43/16* (2013.01); *A61L 29/16* (2013.01); *A61L 2300/404* (2013.01); *A61K 9/0053* (2013.01); *C12N 9/90* (2013.01); *A61L 29/085* (2013.01); *C08L 5/00* (2013.01); *A01N 63/02* (2013.01)
USPC .............. 424/400; 424/48; 424/49; 435/101; 435/252.33; 435/254.2; 435/320.1; 435/325; 435/348; 435/358; 435/369; 514/54; 536/123.1

(58) Field of Classification Search
None
See application file for complete search history.

(56) References Cited

PUBLICATIONS

Fine, D.H. et al., Tenacious adhesion of *Actinobacillus actinomycetemcomitans* strain CU1000 to salivary-coated hydroxyapitate, Arch. Oral Biol. 44(12) (1999) 1063-1076 (abstract only).
Fonzi, W.A. et al., Isogenic Strain Construction and Gene Mapping in *Candida albicans*, Genetics 134 (1993) 717-728.
Horsburgh, M.J. et al., SigmaB Modulates Virulence Determinant Expression and Stress Resistance: Cahracterization of a Functional rsbU Strain Derived from *Staphylococcus aureus* 8325-4, Journal of Bacteriology 184(19) (2002) 5457-5467.
Izano, E.A. et al., Differential Roles of Poly-N-Acetylglucosamine Surface Polysaccharide and Extracellular DNA in *Staphylococcus aureus* and *Staphylococcus epidermidis* Biofilms, Appl. Environ. Microbiol. 74(2) (2008):470-476.
Kadouri, D. et al., Vulnerability of Pathogenic Biofilms to *Micavibrio aeruginosavorus*, Appln. Environ. Microbiol. 73(2) (2007), 605-614 (abstract only).
Kaplan, J.B. et al., Enzymatic Detachment of *Staphylococcus epidermidis* Biofilms, Antimicrobial Agents and Chemotherapy 48 (2004) 2633-2636.
Kehl-Fie, T.E. et al., Examination of Type IV Pilus Expression and Pilus-Associated Phenotypes in *Kingella kingae* Clinical Isolates, Infect. Immun. 78(4) (2010)1692-1699 (abstract only).
Kim, Y. et. al., Released exopolysaccharide (r-EPS) produced from probiotic bacteria reduce biofilm formation of enterohemorrhagic *Escherichia coli* O157:H7. Biochem. Biophys. Res. Comm. 379(2) (2009) 324-329 (abstract only).
Molecular Cloning: A Laboratory Manual, 2nd Ed., vols. 1, 2 and 3 (1989) (abstract only).
Qin, Z. et al., *Pseudomonas aeruginosa* extracellular products inhibit staphylococcal growth, and disrupt established biofilms produced by *Staphylococcus epidermidis*, Microbiology 155:21 (2009) 2148-2156.
The Bacterial Carbohydrate Structure Database v.3 (www.glyco.ac.ru/bcsdb3/).
Valle, J. et. al., Broad-spectrum biofilm inhibition by a secreted bacterial polysaccharide, Proc. Nat. Acad. Sci. U.S.A. 103(33) (2006)12558-12563.
Xiong, Y.Q. et al., Real-Time in Vivo Biolumescent Imaging for Evaluating the Efficacy of Antibiotics in a Rat *Staphylococcus aureus* Endocarditis Model, Antimicrobial Agents and Chemotherapy. 49(1) (2005):380-387.
Yanisch-Perron, C. et al., Improved M13 phage cloning vectors and host strains: nucleotide sequences of the M13mp18 and pUC19 vectors, Gene 33(1) (1985) 103-119 (abstract only).

*Primary Examiner* — Carlos Azpuru
*Assistant Examiner* — David Browe
(74) *Attorney, Agent, or Firm* — Fox Rothschild LLP

(57) ABSTRACT

Polysaccharide-containing extracts isolated from a host cell containing nucleotide sequences encoding genes pamA, pamB and pamC, wherein the extract is capable of inhibiting biofilm formation produced by gram-negative bacteria, gram-positive bacteria and fungi, and methods to inhibit biofilm formation or remove biofilms that have already formed.

6 Claims, 7 Drawing Sheets

FIGURES 1 A-D
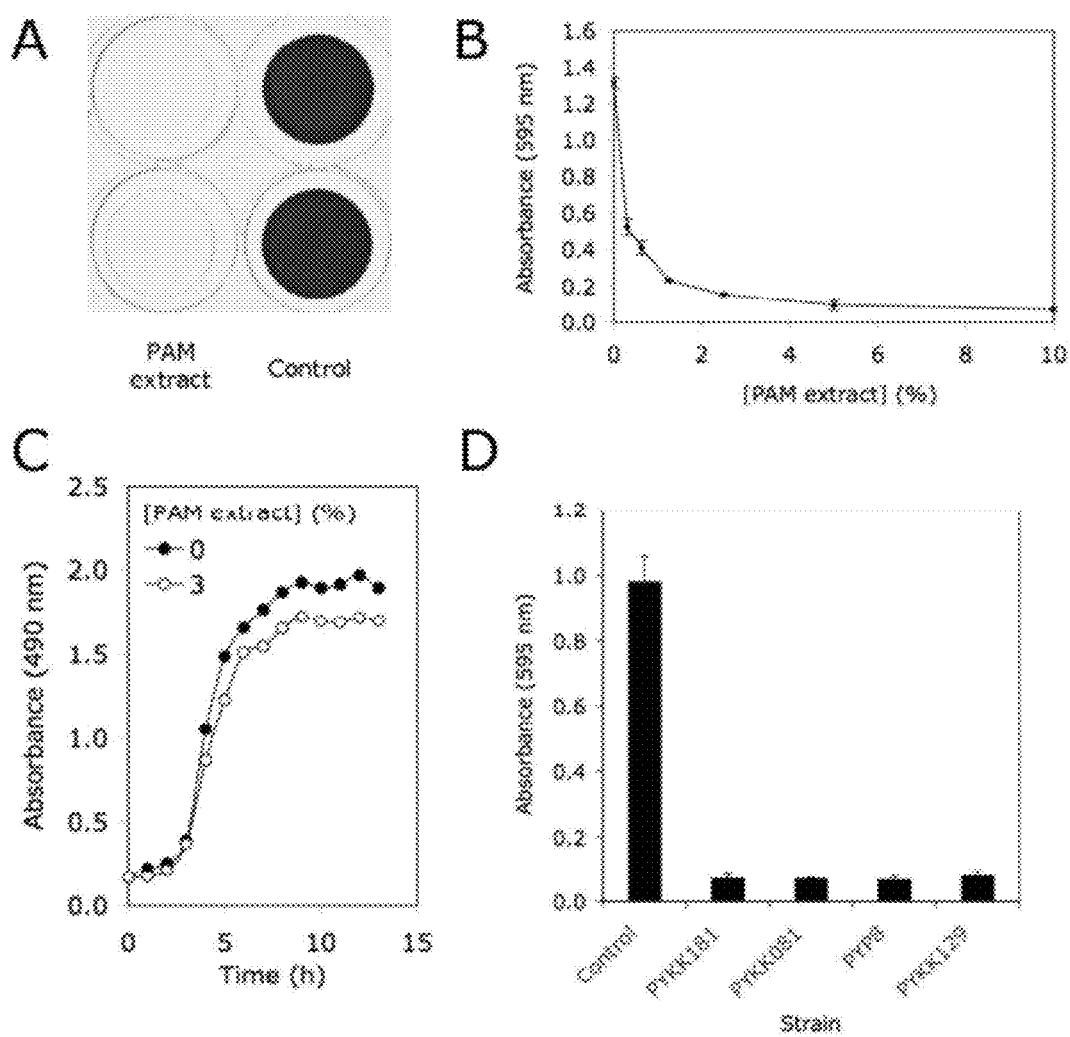

FIGURES 2 A-B
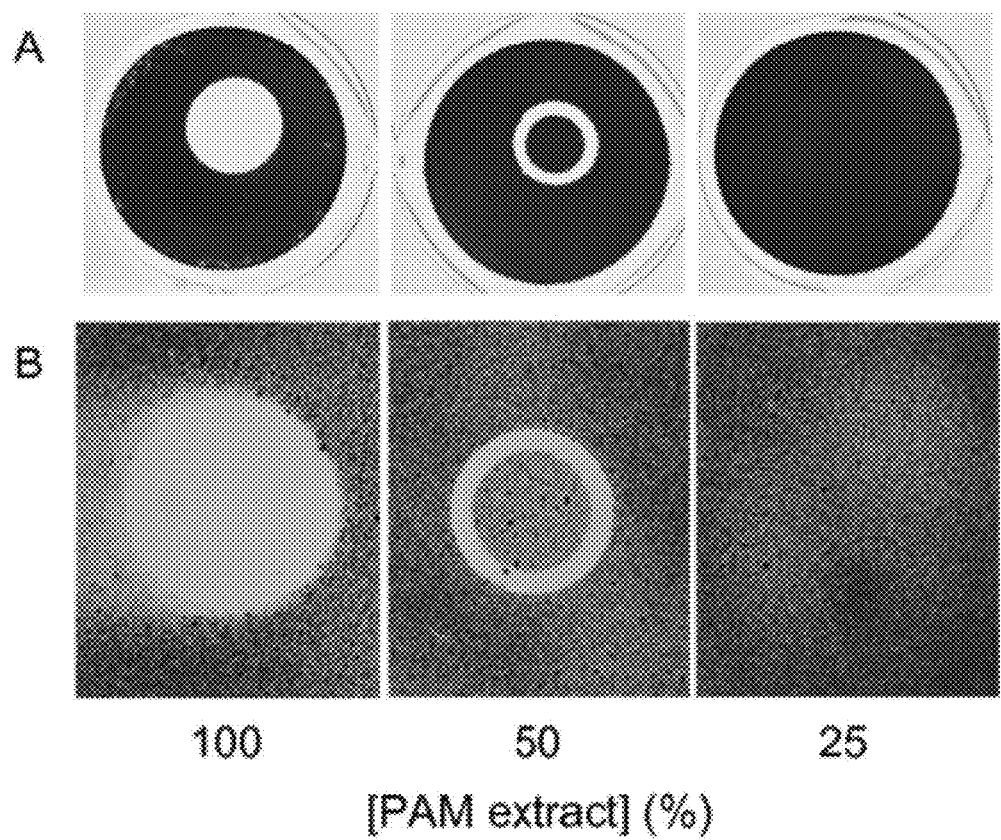

FIGURES 3 A-D
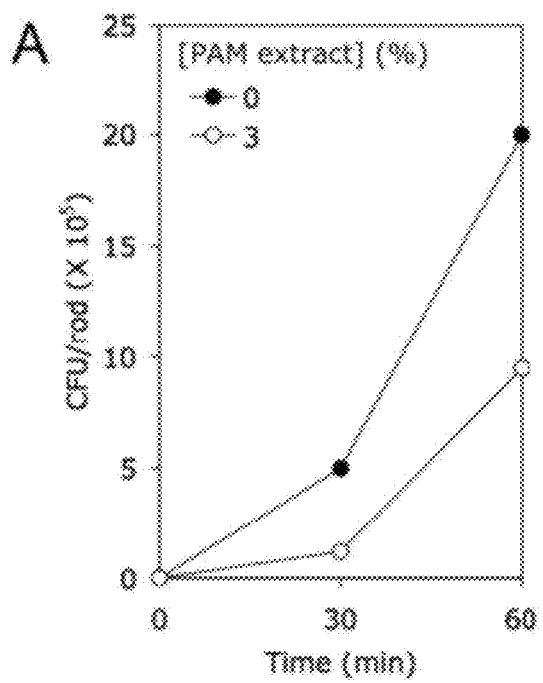
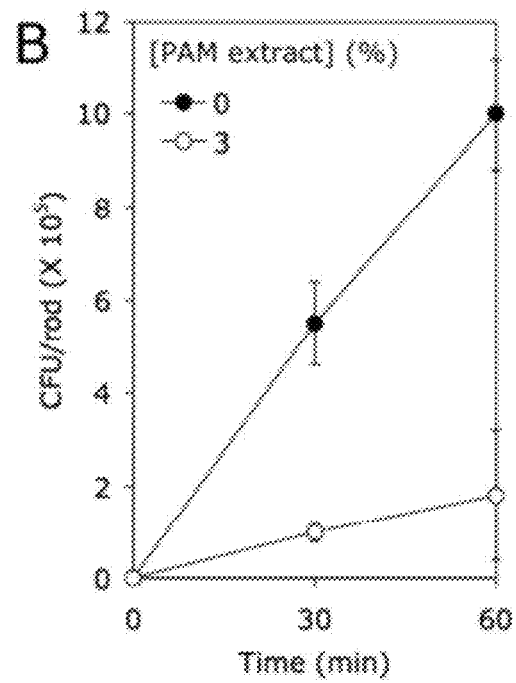
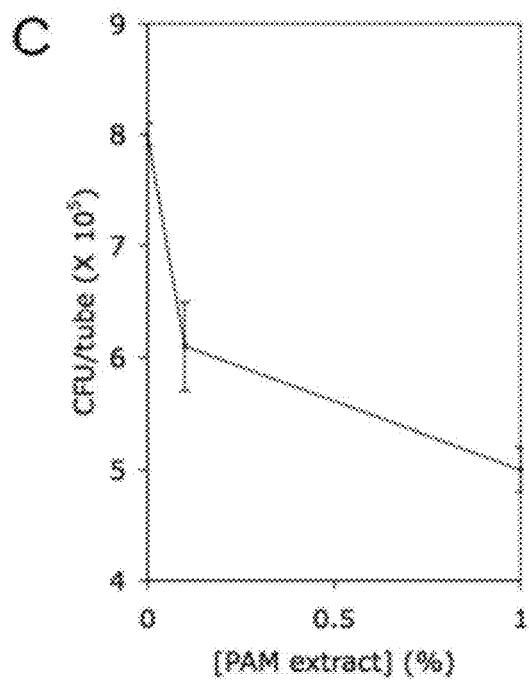
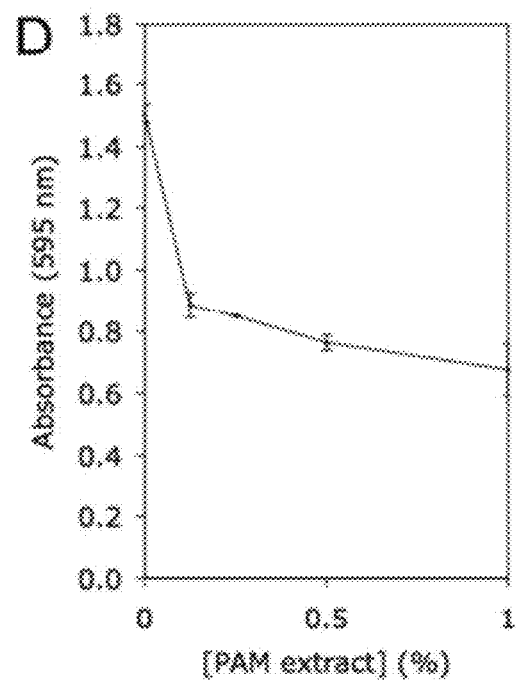

FIGURES 4 A-D
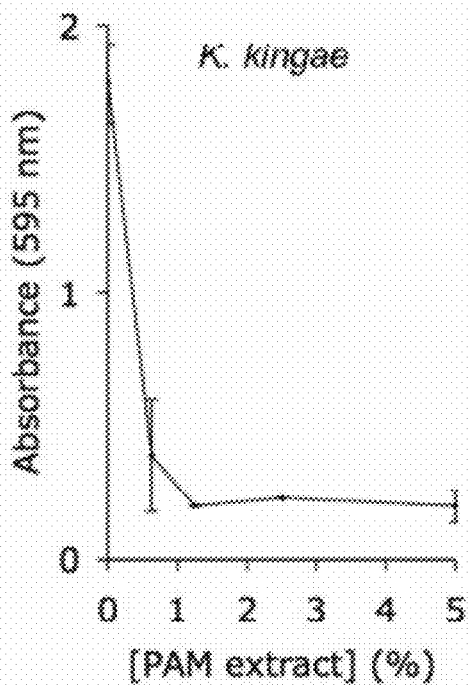
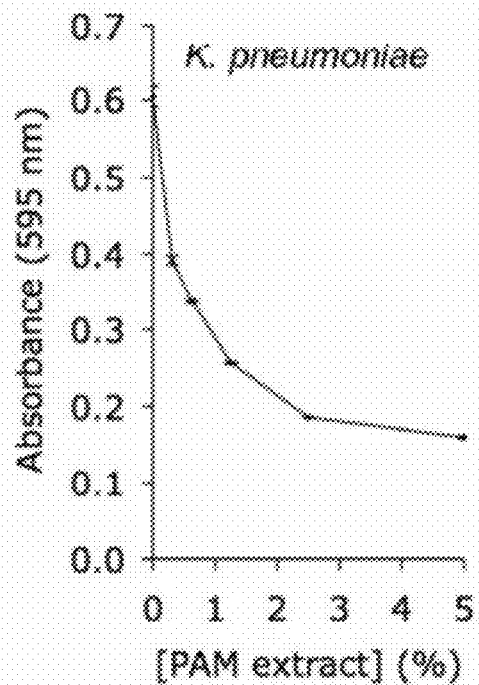
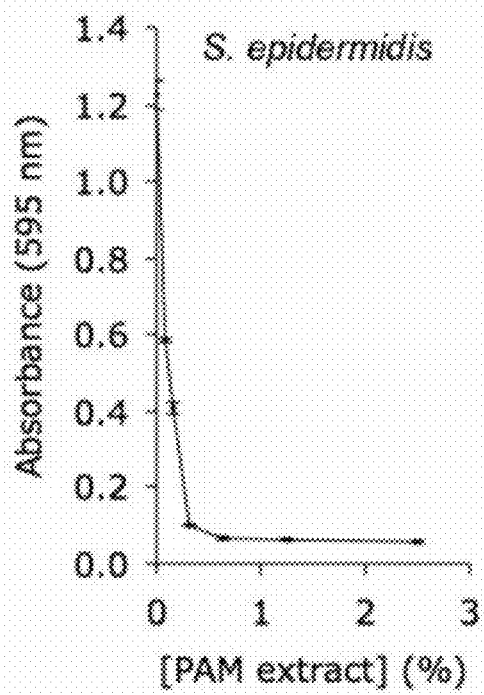
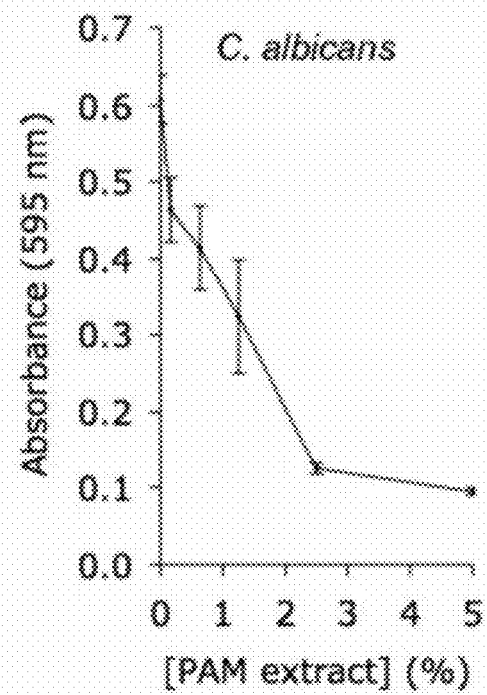

FIGURES 6 A-C
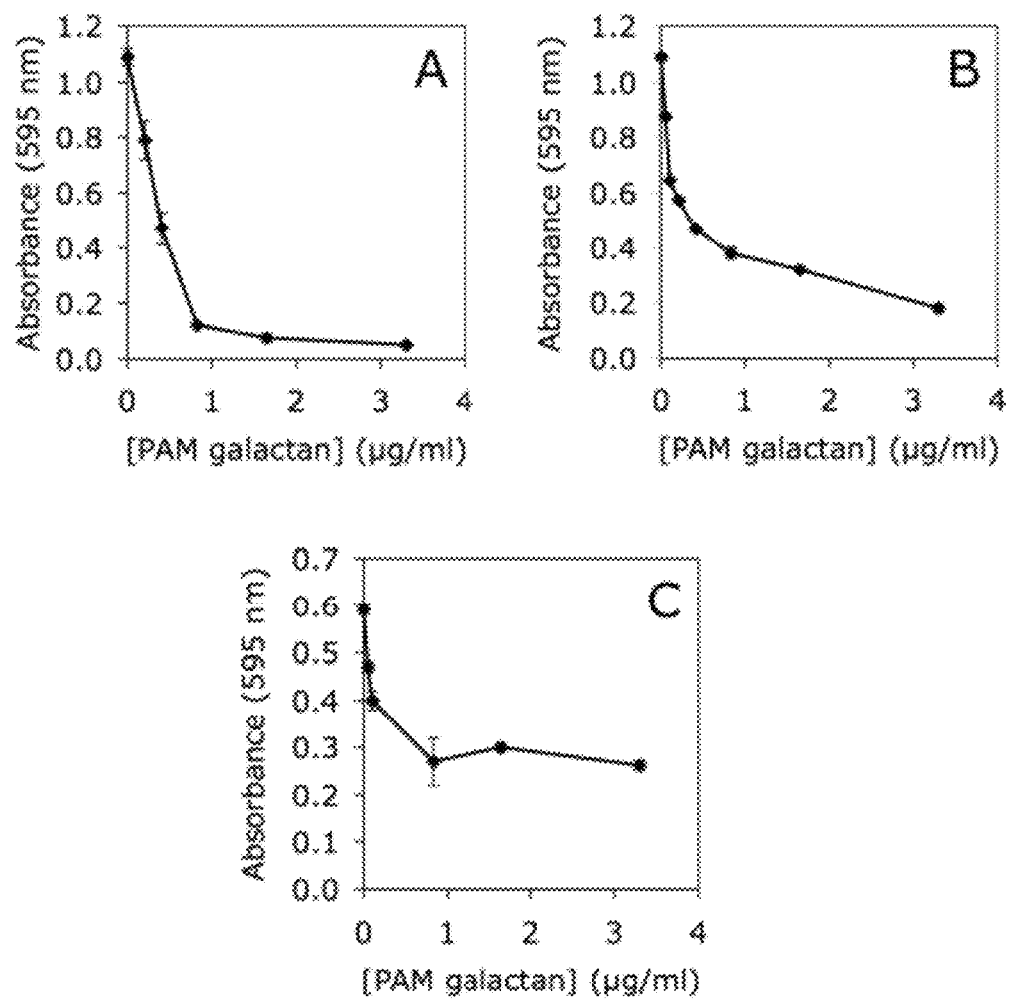

FIGURES 7 A-C
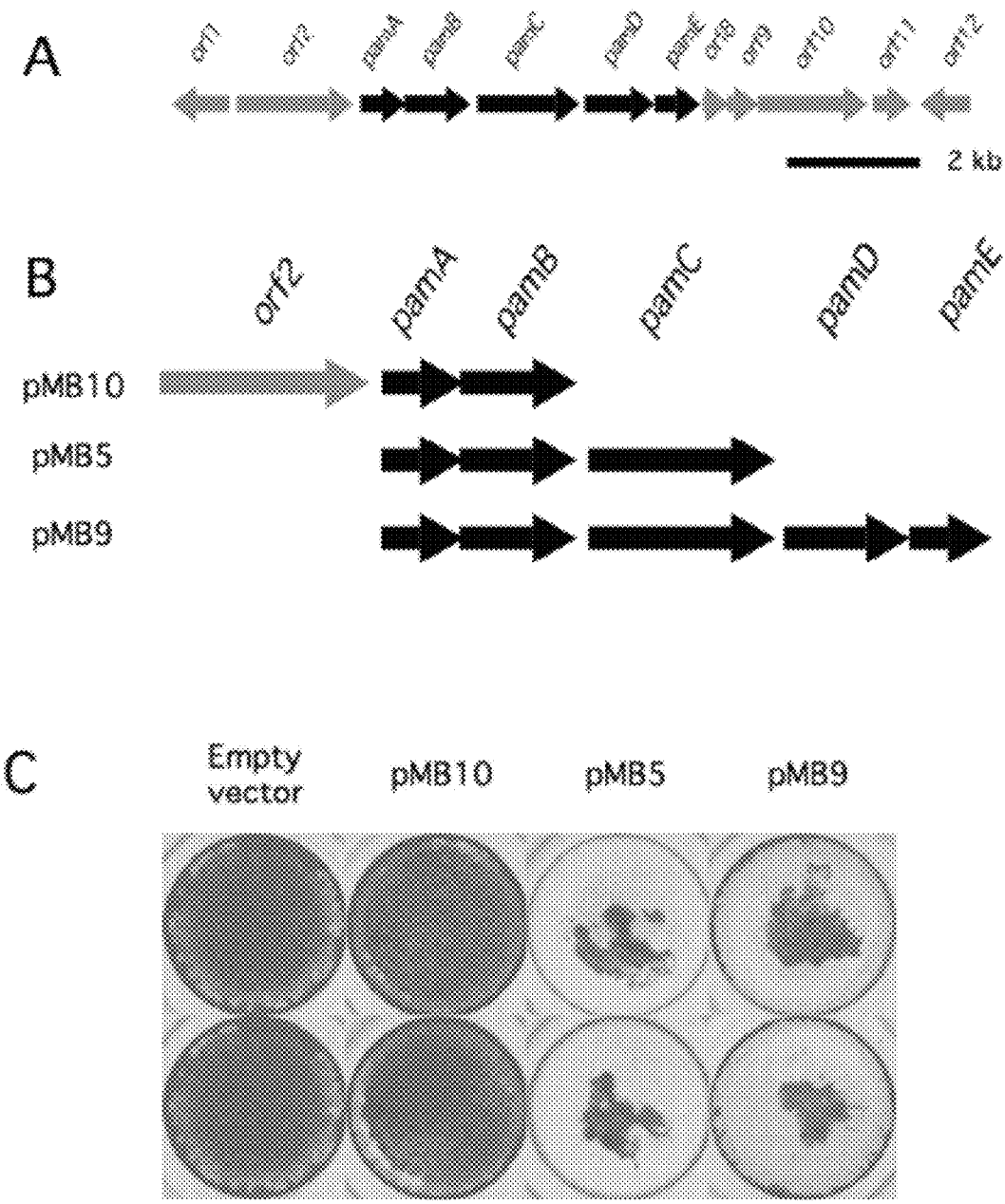

US 8,906,393 B2

BIOFILM INHIBITING COMPOSITION

CROSS REFERENCE TO RELATED APPLICATION

This application claims priority of U.S. Provisional Application No. 61/436,411 filed on Jan. 26, 2011. The content of the application is incorporated herein by reference in its entirety.

GOVERNMENT SUPPORT

The work described herein was funded, in whole or in part, by grant number AI082392, AI080606, and AI080844 from the National Institutes of Health. The United States Government has certain rights in the invention.

FIELD OF THE INVENTION

The present invention relates to novel compositions that inhibit the formation of biofilms by bacterial and fungal cells and promotes the detachment of bacterial cells from a surface, and methods of use thereof.

BACKGROUND OF THE INVENTION

Biofilm is the predominant mode of growth for bacteria in most environments. Biofilms typically contain millions of tightly-packed bacterial cells encased in a polymeric matrix and attached to a tissue or surface. The biofilm mode of growth protects the bacterial cells from cell stressors such as desiccation, predators and antibiotics. Biofilms cause corrosion and biofouling of industrial equipment and chronic infections in clinical settings. Infections stemming from the use of medical devices can lead to potentially life-threatening systemic infections and device malfunction that may require device removal. These device-related infections can be caused by a variety of bacteria, including *Staphylococcus aureus* and *Candida albicans*. There remains a serious need for an effective method of preventing or mitigating medical and surgical device-related bacterial infections.

*Kingella kingae* is a gram-negative bacterium that is a member of the Neisseriaceae family and is closely related to *Neisseria meningitidis*. *K. kingae* colonizes the posterior pharynx of young children (12 to 24 months) and is a common etiology of pediatric infections including septic arthritis, osteomyelitis, and endocarditis. *K. kingae* is also a member of the clinically important HACEK group of bacteria (*Haemophilus parainfluenzae, Aggregatibacter* spp., *Cardiobacterium hominus, Eikenella corrodens, Kingella kingae*). These gram-negative organisms are considered normal flora of the human oral cavity but can infrequently enter the submucosa and cause extraoral infections including endocarditis, bacteremias, and abscesses.

In a screen for novel antibiofilm compounds, potent biofilm inhibition activity in cell-free extracts prepared from colony biofilms produced by the Gram-negative oral bacterium *Kingella kingae* were observed. Preliminary characterization of this extract indicated that it contained abundant DNA, and it was therefore named Polydeoxyribonucleic acid-containing Anti-adhesive Material extract (hereafter referred to as PAM extract). PAM extract exhibits surfactant-like properties, inhibits biofilm formation by a phylogenetically diverse bacteria and fungi, and contains a novel galactan (hereafter referred to as PAM galactan) as one of its active components. The present invention provides compositions comprising PAM galactan and PAM extract and methods of use to prevent biofilm formation on various objects.

SUMMARY OF THE INVENTION

The present invention fills at least the foregoing needs of inhibiting the formation of biofilm produced by bacteria by providing compositions comprising a linear polysaccharide comprising →3)-β-D-Galf-(1→6)-β-D-Galf-(1→ subunits The present invention further provides that the polysaccharide is isolated from a host cell, the host cell comprises nucleic acid sequences encoding genes pamA, pamB and pamC, and the genes direct the biosynthesis of the polysaccharide comprising →3)-β-D-Galf-(1→6)-β-D-Galf-(1→ subunits. In certain embodiments the host cell is a *Kingella kingae* bacterial cell or an *E. coli* bacterial cell. In additional embodiments, strains of *K. kingae* include PYKK081, PYKK181, PYP8 and PYKK129.

The present invention further provides a composition comprising a linear polysaccharide comprising →3)-β-D-Galf-(1→6)-β-D-Galf-(1→ subunits and an antibiotic or an antifungal compound, or both an antibiotic and an antifungal compound.

The present invention provides for a pharmaceutical composition comprising a composition comprising a linear polysaccharide comprising →3)-β-D-Galf-(1→6)-β-D-Galf-(1→ subunits and a pharmaceutically acceptable carrier.

In one embodiment, the present invention provides for a pharmaceutical composition formulated for oral administration. In certain embodiment the pharmaceutical composition formulated for oral administration is a lozenge, a mouthwash, or a piece of chewing gum.

In another embodiment, the present invention provides for a pharmaceutical composition formulated for topical administration. In certain embodiments the pharmaceutical composition formulated for topical administration is an ointment, a cream, or a lotion.

The present invention provides for a medical device coated with a composition comprising a linear polysaccharide comprising →3)-β-D-Galf-(1→6)-β-D-Galf-(1→ subunits.

In certain embodiments the medical device is a central venous catheter, an intravascular catheter, an urinary catheter, a Hickman catheter, a peritoneal dialysis catheter, an endotracheal catheter, a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, or a vascular graft.

In another embodiment, the present invention provides that the medical device is a surgical instrument, such as a clamp, forceps, scissor, skin hook, tubing, needle, retractor, scaler, drill, chisel, rasp, or saw.

The present invention further provides for a wound dressing impregnated with a composition comprising a linear polysaccharide comprising →3)-β-D-Galf-(1→6)-β-D-Galf-(1→ subunits. In certain embodiments, the wound dressing is a sponge, gauze, or catheter shield.

The present invention also provides a method for promoting detachment of bacterial or fungal cells from a biofilm comprising contacting said cells with a composition comprising →3)-β-D-Galf-(1→6)-β-D-Galf-(1→ subunits.

The present invention also provides a method for inhibiting the formation of a biofilm on a surface comprising contacting said surface with a composition comprising →3)-β-D-Galf-(1→6)-β-D-Galf-(1→ subunits.

The present invention also provides a method for inhibiting or treating bacterial or fungal infections in a subject in need thereof comprising administering an effective amount of a composition comprising →3)-β-D-Galf-(1→6)-β-D-Galf-(1→ subunits.

The present invention also provides a vector comprising nucleic acid sequences that encode one or more genes selected from the group consisting of pamA, pamB, pamC, pamD and pamE.

The present invention also provides a host cell comprising a vector comprising nucleic acid sequences that encode one or more genes selected from the group consisting of pamA, pamB, pamC, pamD and pamE.

The present invention also provides a method of making a polysaccharide comprising one or more subunits of →3)-β-D-Galf-(1→6)-β-D-Galf-(1→ by expressing the pamABC genes in a host cell.

The present invention also provides a method for inhibiting the formation of a biofilm on a surface in contact with biofilm producing bacterial cells, comprising contacting said surface with a composition comprising →3)-β-D-Galf-(1→6)-β-D-Galf-(1→ subunits.

The present invention also provides a method for inhibiting or treating bacterial infections in a subject in need thereof comprising administering an effective amount of the pharmaceutical composition comprising a composition comprising →3)-β-D-Galf-(1→6)-β-D-Galf-(1→ subunits.

BRIEF DESCRIPTION OF THE DRAWINGS

FIGS. 1A-D depict inhibition of *S. aureus* biofilm formation by *K. kingae* PAM extract. FIG. 1A depicts biofilm formation by *S. aureus* SH1000 in 96-well microtiter plate wells in the presence or absence of 10% PAM extract. Biofilms were stained with crystal violet. Duplicate wells are shown. FIG. 1B is a histogram representing biofilm formation by *S. aureus* in the presence of increasing concentrations of PAM extract. Biofilm biomass was quantitated by destaining the biofilm and measuring the absorbance of the crystal violet solution. Values show mean absorbance and range for duplicate wells. FIG. 1C is a histogram representing growth of bioluminescent *S. aureus* strain Xen29 in the presence or absence of 3% PAM extract. Growth was monitored by measuring bioluminescence over time using an IVIS Lumina II imaging system (Caliper Life Sciences). FIG. 1D is a histogram representing inhibition of *S. aureus* SH1000 biofilm formation by colony biofilm extracts prepared from four *K. kingae* clinical strains. Extracts were tested at a concentration of 10% by vol. Values show mean absorbance and range for duplicate wells.

FIGS. 2A and 2B show that polystyrene surfaces coated with PAM extract inhibit biofilm formation. Drops of PAM extract were pipetted onto the surface of a 24-well microtiter plate and allowed to evaporate. In some wells the PAM extract was diluted with 1 or 3 vol of water. Wells were then inoculated with *S. epidermidis* in FIG. 2A or according to FIG. 2B, *A. actinomycetemcomitans* and incubated at 37° C. After 18 h, wells were rinsed with water and stained with crystal violet.

FIGS. 3A-D are histograms that demonstrate that PAM extract inhibits *S. aureus* surface attachment and disperses pre-formed *S. aureus* biofilms. FIG. 3A is a histogram representing binding of *S. aureus* cells to stainless steel rods in the presence or absence of 3% PAM extract and FIG. 3B is a histogram representing polystyrene rods in the presence or absence of 3% PAM extract. Values show mean CFU/rod and range for duplicate rods. FIG. 3C is a histogram representing binding of *S. aureus* cells to polycarbonate tubes in 15 min in the presence of 0, 0.1 or 1% PAM extract. Values show mean CFU/tube and range for duplicate tubes. FIG. 3D is a histogram representing detachment of 18-hour-old *S. aureus* biofilms by PAM extract. Biofilms were rinsed with water and treated with the indicated concentration of PAM extract for 1 h. Biofilms were then rinsed with water and quantitated by crystal violet staining. Values show mean absorbance and range for duplicate wells.

FIG. 4 is a histogram demonstrating that PAM extract inhibits biofilm formation by *K. kingae*, *K. pneumoniae*, *S. epidermidis* and *C. albicans*. Biofilms were cultured in 96-well microtiter plates and stained with crystal violet. Values shown mean absorbance and range for duplicate wells.

FIGS. 6A-C are histograms representing inhibition of *S. aureus* SH1000 (FIG. 6A), *K. kingae* PYKK181 (FIG. 6B) and *K. pneumoniae* 1840 (FIG. 6C) biofilm formation by purified *K. kingae* PAM galactan. Biofilm biomass was quantitated by crystal violet staining. Graphs show mean crystal violet absorbance values and range for duplicate wells.

FIGS. 7A-C depict expression of the *K. kingae* pam genes in *E. coli*. FIG. 7A depicts a genetic map of the *K. kingae* pam genes and surrounding region. Arrows indicate open reading frames and direction of transcription. Scale bar=2 kb. FIG. 7B depicts genetic maps of expression plasmid inserts. FIG. 7B depicts inhibition of *S. aureus* biofilm formation by colony biofilm extracts isolated from plasmid-harboring *E. coli* strains. Biofilm were stained with crystal violet and photographed. Duplicate wells are shown.

DETAILED DESCRIPTION OF THE INVENTION

Figure 5:
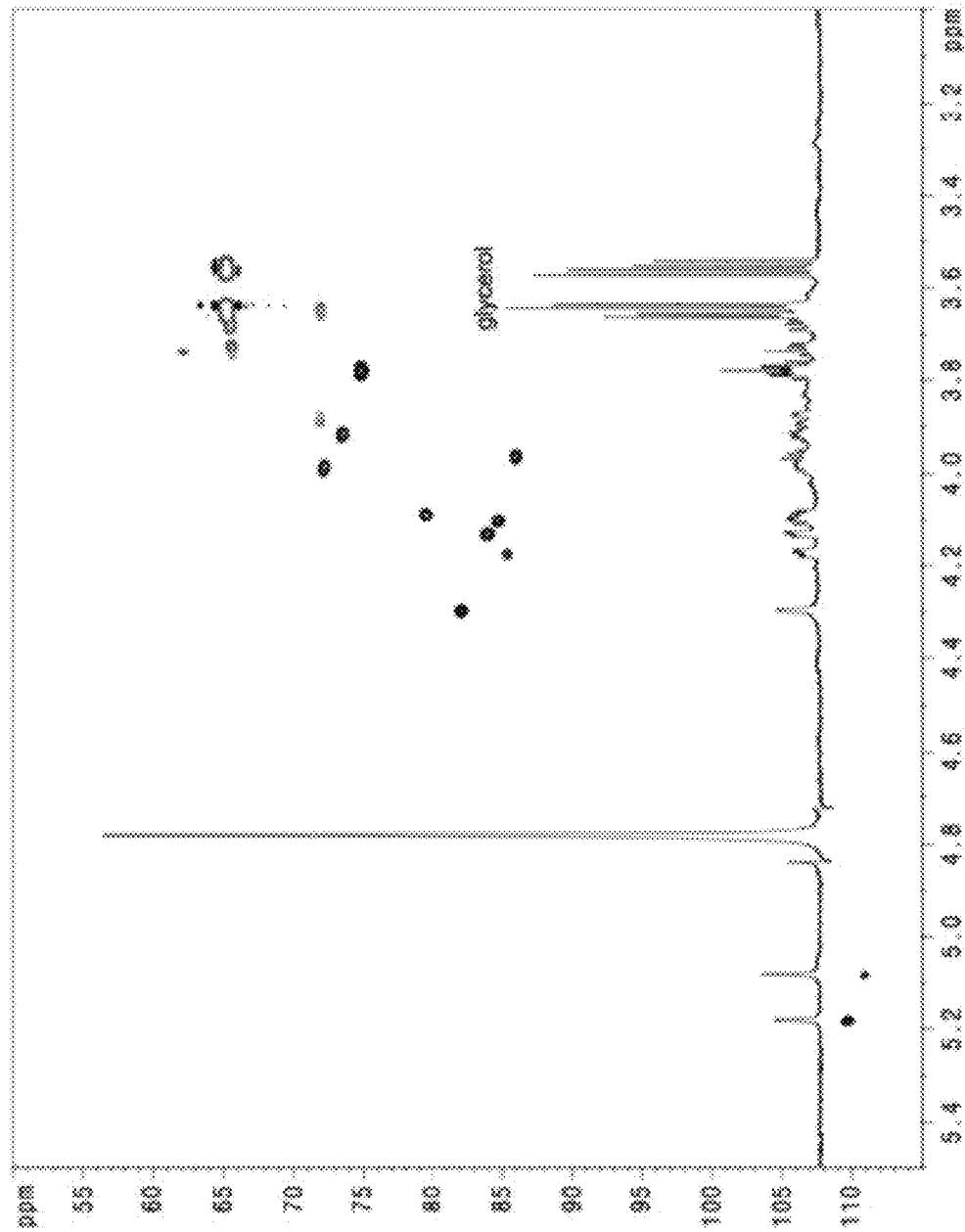
FIG. 5 represents nuclear magnetic resonance (NMR), $^1$H-$^{13}$C HMQC (heteronuclear multiple-quantum coherence) spectrum of PAM extract from *K. kingae* strain PYKK181.

In one embodiment, the present invention relates to compositions comprising a polysaccharide that comprises galactofuranose residues in alternating β(1→3)-β(1→6) linkages. The compositions are useful to inhibit biofilm formation by a broad spectrum of microbial species. The invention further relates to medical devices coated with the composition, wound dressings impregnated with the composition, pharmaceutical compositions for oral and topical administration, methods for inhibiting biofilm formation, methods for promoting detachment of bacterial or fungal cells from a biofilm, and methods for inhibiting and treating bacterial and fungal infections in a subject, as well as vectors comprising sequences that encode a gene cluster that can be transferred to a host cell which can then produce a polysaccharide comprising galactofuranose residues in alternating β(1→3)-β(1→6) linkages.

Cell-free extracts prepared from *Kingella kingae* colony biofilms were found to inhibit biofilm formation by *Aggregatibacter actinomycetemcomitans*, *Klebsiella pneumoniae*, *Staphylococcus aureus*, *S. epidermidis*, *Candida albicans* and *K. kingae*. The extracts inhibited biofilm formation by modifying the physicochemical properties of the cell surface, the biofilm matrix, and the substrate. Chemical and biochemical analyses indicated that the biofilm inhibition activity in the *K. kingae* extract was due to polysaccharide.

Structural analyses showed that the extract contained two major polysaccharides. One was a linear polysaccharide with the structure →6)-α-D-GlcNAcp-(1→5)-β-D-OclAp-(2→, which was identical to a capsular polysaccharide produced by *Actinobacillus pleuropneumoniae* serotype 5. The second was a novel linear polysaccharide, designated PAM galactan, with the structure →3)-β-D-Galf-(1→6)-β-D-Galf-(1→. Purified PAM galactan exhibited broad spectrum biofilm inhibition activity. A cluster of three *K. kingae* genes encoding UDP-galactopyranose mutase (ugm) and two putative galactofuranosyl transferases was sufficient for the synthesis of PAM galactan in *E. coli*. PAM galactan is one of a growing number of bacterial polysaccharides that exhibit antibiofilm activity.

Definitions

As used herein, the singular forms "a," "an" and "the" include plural references unless the content clearly dictates otherwise.

The term "about", as used here, refers to +/−10% of a value.

The term "PAM" is an acronym for Polydeoxyribonucleic acid-containing Anti-adhesive Material.

The term "PAM galactan" as used herein, means a linear polysaccharide comprising galactofuranose residues in alternating β(1→3)-β(1→6) linkages, and is used interchangeably with →3)-β-D-Galf-(1→6)-β-D-Galf-(1→.

The term "PAM extract" as used herein, is a cell-free extract isolated from a host cell wherein said cell comprises nucleotide sequences encoding genes pamA, pamB and pamC, wherein said extract is capable of inhibiting biofilm formation produced by gram-negative bacteria, gram-positive bacteria and fungi, and said extract is capable of promoting detachment of a biofilm that is attached to a surface and said extract further comprises a linear polysaccharide comprising →3)-β-D-Galf-(1→6)-β-D-Galf-(1→. *K. kingae* is a bacterial cell that can be a source for the PAM extract.

The term "host cell" "as used herein refers to a naturally occurring cell or a transformed cell that contains a vector and supports the replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO, HeLa.

The term "functional" refers to the structural properties of a polypeptide encoded by a gene, and includes a polypeptide that retains the necessary structural properties to perform the activity of the polypeptide encoded by the wild type gene. For example, a mutant pamA polypeptide with certain amino acid substitutions resulting from certain single nucleotide polymorphisms will not operate and function as a glycosyltransferase, and thus is not a functional pamA polypeptide.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "effective amount," "therapeutically effective amount" or "therapeutic effect" refers to an amount of a composition comprising a PAM galactan or PAM extract, or to "treat" or "prevent" a disease or disorder in a subject or mammal. In the case of a bacterial infection or fungal infection, the therapeutically effective amount of the drug has a therapeutic effect and as such can reduce the number of bacterial cells or fungal cells; inhibit or stop bacterial or fungal cells from spreading into peripheral organs including, for example, the spread of infectious bacterial or fungal cells into the blood stream; relieve to some extent one or more of the symptoms associated with the microbial infection; reduce morbidity and mortality; improve quality of life; or a combination of such effects.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. In certain embodiments, a subject is successfully "treated" according to the methods of the present invention if the subject shows a reduction or complete absence of infectious bacterial or fungal cells; improvement in quality of life; or some combination of effects.

As used herein, the term "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length polypeptide or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. The term "gene" encompasses both cDNA and genomic forms of a gene.

The terms "polypeptide", "peptide", and "protein", are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product.

A "recombinant" peptide, polypeptide, or protein refers to a peptide, polypeptide, or protein produced by recombinant DNA techniques; i.e., produced from cells transformed by an exogenous DNA construct encoding the desired peptide, polypeptide, or protein.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

"Stringent hybridization conditions" as used herein refers to conditions under which a first nucleic acid sequence (e.g., probe) hybridizes to a second nucleic acid sequence (e.g., target), such as in a complex mixture of nucleic acids. Stringent conditions are sequence-dependent and may vary in different circumstances, and can be suitably selected by one skilled in the art. Stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01-1.0M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C. However, several factors other than temperature, such as salt concentration, can influence the stringency of hybridization and one skilled in the art can suitably select the factors to accomplish a similar stringency.

"Substantially identical" as used herein refers to that the nucleic or amino acid sequence is at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence. Preferably, such variant nucleic acid and polypeptide sequences will share 75% or more (i.e. 80, 85, 90, 95, 97, 98, 99% or more) sequence identity with the sequences recited in the application. Preferably such sequence identity is calculated with regard to the full length of the reference sequence (i.e. the sequence recited in the application).

"Substantially complementary" as used herein refers to that the nucleic acid sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

The term "transfection" refers to the uptake of foreign DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Cotransfection" refers to the simultaneous or sequential transfection of two or more vectors into a given cell.

The term "vector" refers to a nucleic acid assembly capable of transferring gene sequences to target or host cells (e.g., viral vectors, non-viral vectors, particulate carriers, and liposomes). The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

Compositions Useful for Inhibiting Biofilm Formation

In one embodiment, the present invention provides a composition comprising an extract isolated from a host cell wherein said host cell comprises nucleotide sequences encoding genes pamA, pamB and pamC, wherein said extract is capable of inhibiting biofilm formation produced by gram-negative bacteria, gram-positive bacteria and fungi, and said extract is capable of promoting detachment of a biofilm that is attached to a surface and said extract further comprises a linear polysaccharide comprising →3)-β-D-Galf-(1→6)-→-D-Galf-(1→. The extract is referred to as PAM extract, and may be isolated from *K. kingae* bacteria.

PAM extract may be used to inhibit a broad spectrum of biofilms produced by gram-negative and gram-positive bacterial cells as well as fungal cells. The composition comprising PAM extract can also be used to detach preformed biofilms. As previously discussed PAM extract is a cell-free extract prepared from colony biofilms produced by *K. kingae*, the extract contains PAM galactan and inhibits biofilm formation. One with ordinary skill in the art can determine if the composition is capable of inhibiting biofilm formation by using the biofilm inhibition assay also known as the biofilm formation assay and the biofilm detachment assay which is also described in Izano, E. A., et. al. Differential roles of poly-N-acetylglucosamine surface polysaccharide and extracellular DNA in *Staphylococcus aureus* and *Staphylococcus epidermidis* biofilms. Appl. Environ. Microbiol. 74:470-476, 2008.

The present invention provides compositions that are capable of preventing the formation of biofilms by gram-genative and gram positive bacteria comprising a polysaccharide comprising galactofuranose residues in alternating β(1→3)-β(1→6) linkages, also defined as →3)-β-D-Galf-(1→6)-β-D-Galf-(1→ or PAM galactan. Compositions also include extracts, solutions, formulations containing PAM galactan, including without limitation PAM extract and other extracts isolated from host cells that contain nucleic acids that encode genes pamA, pamB, and pamC. One with ordinary skill in the art can determine if the composition is capable of inhibiting biofilm formation by using the biofilm inhibition assay also known as the biofilm formation assay as described in Izano, E. A., et. al., Differential roles of poly-N-acetylglucosamine surface polysaccharide and extracellular DNA in *Staphylococcus aureus* and *Staphylococcus epidermidis* biofilms. Appl. Environ. Microbiol. 74:470-476, 2008.

PAM galactan may be used to inhibit the formation of a biofilm produced by gram-negative and gram-positive bacteria. *K. pneumoniaeis* and *K. kingae* are examples of gram-negative bacteria, and *S. epidermis* is an example of a gram-positive bacterium. PAM galactan may be purified from a cell free extract prepared from colony biofilms of *K. kingae*.

The present invention also provides for methods of producing a composition comprising PAM galactan and PAM extract. As previously discussed PAM extract is a cell-free extract prepared from colony biofilms produced by *K. kingae*, the extract contains PAM galactan and inhibits biofilm formation. PAM galactan may also be prepared using standard recombinant biotechnology techniques. Pam galactan may also be purified from a host cell transfected with a PAM galactan gene cluster. The PAM galactan gene cluster is a set of genes that is responsible for the biosynthesis of PAM galactan, also referred to as pamABCDE. A host cell may be transfected with a vector containing all or parts of the PAM galactan gene cluster. The host cell should at least contain a nucleic acid sequence that encodes pamA, pamB and pamC. The nucleic acids that encode pamA, pamB, and pamC may be contained in a single vector, or in more than one vector, for example in three expression vectors. An example of a host cell is *E. coli*. Other types and species of host cells are known in the art. For additional guidance, skilled artisans may consult Sambrook et al. (Molecular Cloning, A Laboratory Manual, Cold Spring Harbor Press, Cold Spring Harbor, N.Y., 1989).

Other cells may produce PAM galactan or PAM extract. Homologues of pamABC are present in the genome of the oral bacterium *Simonsiella mulleri*, and a modified pamABC gene cluster containing one additional gene located between pamA and pamB is present in the genome of the swine respiratory pathogen *Actinobacillus* pleuropneumoniae. The present invention also provides for a host cell comprising sequences that encode pamA, pamB, and pamC. The present invention also provides for a host cell comprising sequences that encode pamA, pamB, and pamC. The host cell may further comprise sequences that encode pamD and/or pamE.

In another embodiment, the present invention provides a vector comprising sequences that encode all or part of the PAM galactan gene cluster. The vector may comprise pamA, pamB, pamC, pamD, and/or pamE and be used to transfect a host cell. The nucleic acid sequence that encodes pamA may be substantially identical to SEQ ID. NO. 1 or 5, and encodes a functional glycosyltransferase. The nucleic acid sequence that encodes pamA may be substantially complementary to SEQ ID. NO. 1 or 5. The nucleic acid sequence that encodes pamB may be substantially identical to SEQ ID. NO. 2 or 6 and encodes encodes a functional UDP-galactopyranose mutase. The nucleic acid sequence that encodes pamB may be substantially complementary to SEQ ID. NO. 2 or 6. The nucleic acid sequence that encodes pamC may be substantially identical to SEQ ID. NO. 3 or 7 and encodes a functional glycosyltransferase. The nucleic acid sequence that encodes pamC may be substantially complementary to SEQ ID. NO. 3 or 7. The nucleic acid sequence that encodes pamD may be substantially identical to SEQ ID. NO. 4 or 9 and encodes a functional glycosyltransferase. The nucleic acid sequence that encodes pamD may be substantially complementary to SEQ ID. NO. 4 or 9. The nucleic acid sequence that encodes pamE may be substantially identical to SEQ ID. NO. 5 or 10 and encodes a functional glycosyltransferase. The nucleic acid sequence that encodes pamE may be substantially complementary to SEQ ID. NO. 5 or 10. As will be understood by those with skill in the art reading this disclosure, artificially produced genes that encode functionally equivalent or active variants of pamABCDE proteins can also be produced routinely in accordance with the teachings herein using various well known genetic engineering techniques.

In another embodiment, the present invention provides a composition comprising PAM galactan or PAM extract and may further comprise other polysaccharides that inhibit the formation of biofilms. For example the PAM extract also contains another polysaccharide (PS2) also identified as →6)-β-D-GlcNAcp-(1→5)-β-D-OclAp-(2→, that may contain properties that inhibit biofilm formation. Other bacterial exopolysaccharides also exhibit biofilm inhibition activity. *E. coli* strains that produce group 11 capsular polysaccharide, for example, release a soluble polysaccharide of unknown structure that prevents biofilm formation by a wide range of gram-positive and gram-negative bacteria (Valle, J., et. al., Broad-spectrum biofilm inhibition by a secreted bacterial polysaccharide. Proc. Nat. Acad. Sci. U.S.A. 103:12558-12563, 2006). *Pseudomonas aeruginosa* Pel and Psl exopolysaccharides have been shown to inhibit *S. epidermidis* biofilm formation and disrupt pre-formed *S. epidermidis* biofilms (Qin, Z., et. al., *Pseudomonas aeruginosa* extracellular products inhibit staphylococcal growth, and disrupt established biofilms produced by *Staphylococcus epidermidis*. Microbiology 654 155:2148-2156, 2009). Exopolysaccharides of unknown structure produced by *Lactobacillus acidophilus* A4 were shown to inhibit initial attachment and autoaggregation of *E. coli* O157:H7 during biofilm development, and to inhibit biofilm formation by phylogenetically diverse gram-negative and gram-positive bacteria (Kim, Y., et. al., Released exopolysaccharide (r-EPS) produced from probiotic bacteria reduce biofilm formation of enterohemorrhagic *Escherichia coli* O157:H7. Biochem. Biophys. Res. Comm. 379:324-329, 2009).

In another embodiment, the present invention provides a composition comprising PAM galactan or PAM extract and may further comprise other substances that inhibit the formation of biofilms. For example, a composition comprising PAM galactan or PAM extract may further comprise enzymes such as Dispersin B, DNase I, and quorum-quenching enzymes; quorum-sensing signal molecules such as acyl homoserine lactones, *Pseudomonas* quinolone signal and furanosylborate; glycopeptidolipids; phenazines; fatty acid signals; peptide signals produced by Staphylococci; nitric oxide; D-amino acids or any combination thereof.

In another embodiment, the present invention provides a composition comprising PAM galactan or PAM extract and may further comprise anti-infective agents such as antibiotics and or antifungal compounds. Antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericinB), azoles (e.g. fluconazole) and betalactam inhibitors (e.g. sulbactam), minocycline, rifampin, erythromycin, nafcillin, cefazolin, imipenem, aztreonam, gentamicin, sulfamethoxazole, vanco-mycin, ciprofloxacin, trimethoprim, metronidazole, clindamycin, teicoplanin, mupirocin, azithro-mycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Anti-fungal agents that may be used include amorolfine, isoconazole, clo-trimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc pyrithione, and sodium pyrithione.

In another embodiment, the present invention provides compositions comprising PAM galactan or the PAM extract that are in solution or gel form, or as a component in a formulation for use as a coating or a sealant or in a paste, such as toothpaste. Evaporation coating is a method one with ordinary skill in the art can use to coat objects with PAM galactan or PAM extract. One can determine the concentration of PAM galactan or PAM extract necessary for a solution or formulation to coat an object by using the surface coating assay, whereby objects are coated with the solution or formulation, the solution is evaporated from the object or formulation is dried, the object is immersed in biofilm producing bacteria, the object is then rinsed and stained with Gram's crystal violet, and observed for the presence of any stained biofilms. Other techniques are known in the art to determine whether objects with a coating comprising PAM galactan or the PAM extract retains anti-biofilm forming properties.

PAM galactan or PAM extract may be used as a coating for medical devices and medical intruments to prevent or inhibit bacterial or fungal attachment and reduce the risk of infection. Various types of medical devices include but are not limited to central venous catheters, intravascular catheters, urinary catheters, Hickman catheters, peritoneal dialysis catheters, endrotracheal catheters, mechanical heart valves, cardiac pacemakers, arteriovenous shunts, schleral buckles, prosthetic joints, tympanostomy tubes, tracheostomy tubes, voice prosthetics, penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Examples of medical instruments include but are not limited to clamps, forceps, scissors, skin hooks, tubing, needles, retractors, scalers, drills, chisel's, rasps and saws. One with ordinary skill in the art will recognize other types of medical devices or medical instruments that are exposed to biofilm producing microbes that will benefit from the use of an anti-biofilm formation coating.

PAM galactan or PAM extract may be used in a solution or a formulation to impregnate wound dressings including but not limited to sponges, gauze, adhesive tapes, as well as catheter shields as well other materials used to cover a catheter insertion site, to prevent or inhibit bacterial or fungal attachment and reduce the risk of infection.

PAM galactan or PAM extract may be used in a solution or formulation as a coating or sealant for teeth to prevent or inhibit bacterial or fungal attachment and reduce the risk of infection.

PAM galactan or PAM extract may be used in a solution or formulation as a coating on objects to spatially position bacteria onto surfaces. For example certain types of substrates to culture bacteria such as a petri dish may contain a coating of PAM galactan or PAM extract within a designated surface area on the surface of the dish, thus bacteria that are cultured on the dish are inhibited from producing a biofilm on the designated coated areas of the dish and the bacteria may form colonies on the non-coated areas of the dish. The coating may be useful in the fabrication of biodevices such as biobatteries or biosensors. A biosensor may be a microfluidic device.

Other applications include the use of PAM galactan or PAM extract for use in a solution, formulation or sealant to coat the interior of an object that is immersed in an aqueous environment with microbes, for example a fish tank or an aquarium, to decrease the formation of biofilms on the surface of the object by microbes, and for example decrease algae growth.

PAM galactan or PAM extract may be also be incorporated in a liquid disinfecting solution. Such solutions may further comprise antimicrobials or antifungals such as alcohol, iodine solution and antibiotics as well as preservatives. These solutions may be used as disinfectants of the skin, to disinfect the surfaces of objects or as a cleaning solution.

In another embodiment, the present invention provides methods of inhibiting biofilm formation using the above described compositions comprising PAM galactan or PAM extract. One method comprises adding a composition comprising PAM galactan to a solution or to the surface of an object to prevent the formation of biofilms that may be exposed or contain biofilm producing bacteria. Another method comprises adding a composition comprising PAM extract to a solution or to the surface of an object to prevent the formation of biofilms that may be exposed or contain biofilm producing bacteria or fungi.

In another embodiment, the present invention provides a method to detach pre-formed biofilms. The method comprises contacting a preformed biofilm with the composition comprising PAM extract.

In another embodiment, the present invention provides pharmaceutical compositions comprising isolated PAM galactan and a pharmaceutically acceptable carrier. The invention also provides a pharmaceutical composition comprising PAM extract and a pharmaceutically acceptable carrier. To administer the pharmaceutical composition to a subject, it is preferable to formulate the molecules in a composition comprising one or more pharmaceutically acceptable carriers. The phrase "pharmaceutically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

The pharmaceutical composition may comprise PAM galactan or PAM extract. PAM galactan can be an isolated or purified polysaccharide.

An "isolated" or "purified" polysaccharide refers to a polysaccharide that has been separated from other proteins, lipids, and nucleic acids with which it is naturally associated. The polysaccharide can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by nuclear magnetic resonance. An isolated polysaccharide described in the invention can be purified from a natural source, produced by recombinant DNA techniques, or by chemical methods.

Pharmaceutical formulations suitable for oral administration may be provided in convenient unit forms including, but not limited to, capsules or tablets, each containing a predetermined amount of the PAM galactan or PAM extract; as a powder or granules; as a solution, a suspension or as an emulsion. The PAM galactan or PAM extract can also be presented as an electuary, or paste. Tablets and capsules for oral administration may contain conventional excipients such as binding agents, fillers, lubricants, disintegrants, or wetting agents. The tablets may be coated according to methods well known in the art. Timed release formulations, which are known in the art, may also be suitable. Oral liquid preparations may be in the form of, for example, aqueous or oily suspensions, solutions, emulsions, syrups or elixirs, or may be presented as a dry product for constitution with water or other suitable vehicles before use. Such liquid preparations may contain conventional additives such as suspending agents, non-aqueous vehicles, including edible oils, or preservatives.

For topical administration to the epidermis, PAM galactan or PAM extract of the present invention may be formulated in an ointment, cream, or lotion, or as a transdermal patch. Ointments and creams, may, for example, be formulated with an aqueous or oily base with the addition of suitable thickening and/or gelling agents. Lotions may be formulated with an aqueous or oily base and will in general also contain one or more emulsifying agents, stabilizing agents, suspending agents, thickening agents, or coloring agents. Formulations suitable for topical administration in the mouth include lozenges, or chewing gum comprising PAM galactan or PAM extract in a flavored base, usually sucrose and acacia or tragacanth; pastilles comprising the active ingredient in an inert base such as gelatin and glycerin or sucrose and acacia; and mouth washes comprising the active ingredient in a suitable liquid carrier. For topical administration to the eye, the PAM galactan or PAM extract can be made up in solution or suspension in a suitable sterile aqueous or non-aqueous vehicle. Additives such as buffers (e.g. sodium metabisulphite or disodium edeate) and thickening agents such as hypromellose can also be included.

The amount of PAM galactan or PAM extract of the present invention required for use in treatment will of course vary not only with the PAM galactan or PAM extract selected but also with the route of administration, the nature of the condition being treated, and the age and condition of the subject. Increasing detachment of bacteria from a biofilm is also expected to decrease resistance of the bacteria to antibiotic therapy.

The present invention provides a method of treating a bacterial infections in a subject in need thereof, comprising administering a pharmaceutical composition comprising PAM galactan or PAM extract.

The present invention also provides a method for enhancing efficacy of antibiotic therapy against bacterial infections by administration of a pharmaceutical composition of the present invention in combination with or prior to administration of an antibiotic.

The dose of the pharmaceutical composition of the present invention is determined according to the age, body weight, general health condition, sex, diet, administration time, administration method, clearance rate, and the level of disease for which patients are undergoing treatments at that time, or further in consideration of other factors. While the daily dose of the pharmaceutical composition of the present invention varies depending on the condition and body weight of patient, the kind of the pharmaceutical composition, administration route and the like, for example, 0.01 to 100 mg/patient/day by oral or topical administration.

In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated.

EXAMPLES

The invention now being generally described, it will be more readily understood by reference to the following examples, which are included merely for purposes of illustration of certain aspects and embodiments of the present invention, and are not intended to limit the invention.

Those skilled in the art will recognize, or be able to ascertain using no more than routine experimentation, many equivalents to the specific embodiments of the invention described herein. Such equivalents are intended to be encompassed by the following embodiments.

Example 1

Materials and Methods

Strains and culture conditions. The strains used in this study were *K. kingae* PYKK081, PYKK181, PYP8 and PYKK129 (Kehl-Fie 2010, Infect. Immun. 78:1692-1699); *S. aureus* SH1000 (Horsburgh 2002, J. Bacteriol. 184:5457-5467); *S. aureus* Xen29 (Xiong 2005, Antimicrob. Agents Chemother. 49:380-387); *S. epidermidis* NJ9709 (Kaplan 2004, Antimicrob. Agents Chemother. 48:2633-2636); *Aggregatibacter actinomycetemcomilans* CU 1000 (Fine 1999, Arch. Oral Biol. 44:1063-1076); *Klebsiella pneumoniae* 1840 (Kadouri 2007, Appl. Environ. Microbiol. 73:605-614); *E. coli* JM109 (Yanisch-Perron 1985, Gene 33:103-119); and *Candida albicans* CAF2-1 (Fonzi 1993, Genetics 134:717-728). *K. pneumoniae* and *E. coli* were cultured in LB, *C. albicans* was cultured in Tryptic soy broth (TSB) supplemented with 10% fetal bovine serum, and all other bacteria were cultured in TSB supplemented with 6 g/l yeast extract and 8 g/l glucose. All cultures were incubated at 37° C. *K. kingae* and *A. actinomycetemcomilans* cultures were incubated in 10% $CO_2$.

Preparation of *K. kingae* colony biofilm extracts. Extracts were prepared from bacterial lawns (colony biofilms) cultured on Tryptic soy agar plates. Lawns were prepared by spreading 109-1010 CFUs directly onto the surface of the plate, and incubating the plate for 2 d. The cell paste was scraped from the surface of the plate with a cell scraper, transferred to a polycarbonate thick walled centrifuge tube (Sorvall no. 03237), and subjected to ultracentrifugation at 115,000×g for 15 min. The supernatant was transferred to a new tube and sterilized by passage through a 0.22-µm cellulose acetate centrifuge tube filter (Costar #8160). The resulting extract, termed PAM extract, was stored at 4° C.

Biofilm inhibition assay. Biofilms were cultured in 96-well polystyrene microtiter plates as previously described. Briefly, cells were diluted to 104 to 105 108 CFU/ml in TSB supplemented with 0.1 vol of PAM extract, or 0.1 vol of water as a control. Aliquots of cells (200 µl each) were transferred to the wells of a microtiter plate, and the plate was incubated at 37° C. for 18 h. Biofilms were washed with water and stained for 1 min with 200 µl of Gram's crystal violet. Stained biofilms were rinsed with water and dried. The amount of crystal violet binding was quantitated by destaining the biofilms for 10 min with 200 µl of 33% acetic acid, and then measuring the absorbance of the crystal violet solution at 595 nm. All assays were performed 3-5 times with similarly significant decreases in absorbance values.

Surface attachment assays. Single-cell suspensions of *S. aureus* strain SH1000 were prepared using a filtration protocol as previously described. Aliquots of cells (0.5-ml each, ca. $10^7$-$10^8$ CFU/ml) were transferred to 1.5-ml polypropylene microcentrifuge tubes. Cell suspensions were supplemented with 0.03 vol of K. kingae biofilm extract, or 0.03 vol of water as a control. Stainless steel rods (0.6-mm diam×13-mm length) or polystyrene rods (1.4-mm diam×15-mm length) were then placed in the tubes, and the tubes were incubated at 37° C. After 30 or 60 min, the rods were removed from the tubes, rinsed three times with phosphate buffered saline (PBS), and transferred to a 15-ml conical centrifuge tube containing 1 ml of PBS. The rods were sonicated on ice (2×30 sec) using an IKA Labortechnik sonicator set to 50% power and 50% duty cycle. CFUs in the sonicate were quantitated by dilution plating. In another experiment, S. aureus single-cell suspensions were supplemented with 0.01 or 0.1 vol of K. kingae biofilm extract, and then 1-ml aliquots of cells were transferred to 15-ml polycarbonate tubes. After 15 min, the cells were removed from the tubes, and the tubes were rinsed three times with PBS. One ml of PBS was then added to each tube, the tubes were sonicated as described above, and CFUs in the sonicate were quantitated by dilution plating. All assays were performed 3-5 times with similarly significant decreases in absorbance values.

Surface coating assay. A volume of 10 µl of PAM extract (or 10 µl of water as a control) was transferred to the center of a well of a 24-well tissue-culture-treated polystyrene microtiter plate (Falcon no. 353047). The plate was incubated at 37° C. for 30 min to allow complete evaporation of the liquid. The wells were then filled with 1 ml of TSB containing $10^4$ to $10^5$ CFU/ml of S. epidermidis or A. actinomycelemcomitans. After 18 h, biofilms were rinsed with water and stained with 1 ml of Gram's crystal violet. Stained biofilms were rinsed with water and dried, and the wells were photographed.

Chemical analysis of PAM extract. For enzymatic treatments, crude colony biofilm extracts were incubated for 1 h at 37° C. with 100 µg/ml DNase I, RNase A, or proteinase K (Sigma-Aldrich). For ether extraction, an equal volume of ether was added to the PAM extract, and the tube was mixed by vortex agitation for 15 sec. The ether layer was removed with a pipette and discarded, and the residual ether was allowed to evaporate for 15 min at room temperature. For sodium metaperiodate treatment, 0.1 vol of 100 mM sodium metaperiodate was added to the PAM extract, and the extract was incubated at 37° C. for 1 h. Molecular weights were determined using Microcon centrifugal concentrators (Millipore) with 10-kDa, 30-kDa, and 100-kDa molecular weight cut-off filters.

Analytical techniques. Pam extract was treated with DNase I and RNase A (100 µg/ml each; 1 h, 37° C.) and passed through a 100-kDa molecular weight cut-off cellulose centrifugal filter (Amicon no. UFC81008). The retenate was lyophilized, and the residue was dissolved in $D_2O$. The precipitate was removed by centrifugation, and the resulting supernatant was analyzed by NMR spectroscopy. Galactofuranose residues were identified on the basis of $^{13}C$ NMR chemical shifts. Structures were confirmed by spectra simulation using the Bacterial Carbohydrate Structure Database v.3 (www.glyco.ac.ru/bcsdb3/). Linkage positions were identified on the basis of NOE and HMBC correlations, and by methylation analysis. Identity of galactose was confirmed by monosaccharide analysis.

Purification of PAM galactan. PAM extract was treated with DNase and RNase, filtered and lyophilized as described above. The residue was resuspended in 2% acetic acid and heated at 100° C. for 3 h. The precipitate was removed by ultracentrifugation at 100,000×g for 3 h. The supernatant was fractionated by Sephadex G-50 column chromatography in pyridine-acetic acid buffer (4 ml/l of pyridine and 1% acetic acid). The eluate was monitored by refractive index and collected fractions (10 ml) were analyzed by thin layer chromatography on $SiO_2$ plates. Spots were visualized with 5% $H_2SO_4$ in ethyl alcohol.

Cloning and sequencing the K. kingae pam genes. Genomic DNA was isolated from K. kingae strain PYKK181 using a DNeasy Blood & Tissue kit (Qiagen). The DNA was amplified by PCR using primers that amplify orf2pamAB, pamABC, and pamABCDE (as shown in FIG. 7B). The DNA was amplified by PCR using primer pairs F1 (5-TGGTAG-GCAAAGTTTGCG-3 (SEQ ID NO. 11)) and R1 (5-CG-TACCACCCCAATAACG-3 (SEQ ID NO: 15)); F2 (5-TTGATGAATGCAGTGGCG -3 (SEQ ID NO: 12)) and R2 (5-ATGCCGCCTGTTATTAGCC-3(SEQ ID NO: 13)); and F2 and R3 (5-TGCCTTCGGTGTGAAAGG-3 (SEQ ID NO: 14)). The PCR products were cloned into plasmid vector pGEM-T (Promega), resulting in plasmids pMB10, pMB5 and pMB9, respectively. The nucleotide sequences of both strands of the plasmid inserts were determined using an ABI 3130x1 Genetic Analyzer.

Expressing the K. kingae pam genes in E. coli. Plasmids pGEM-T, pMB10, pMB5 and pMB9 were transformed into E. coli strain JM109. Transformants were selected on agar supplemented with 50 µg/ml ampicillin. Lawns of transformants were grown on agar plates supplemented with 50 µg/ml ampicillin and 1 mM IPTG. Lawns were harvested and cell-free extracts were prepared by ultracentrifugation as described above. Extracts were sterilized by passage through a 0.22-µm filter, incubated at 100° C. for 15 min, and then tested for activity in the biofilm inhibition assay described above.

Nucleotide sequence accession numbers. The nucleotide sequences of the pamABC gene clusters from K. kingae strains PYKK081 and PYKK181 are shown in FIGS. 10 and 11, respectively.

Example 2

K. Kingae PAM Extract Inhibits S. Aureus Biofilm Formation

A cell-free extract prepared from colony biofilms of K. kingae clinical strain PYKK181 (hereafter referred to as K. kingae PAM extract) was tested for its ability to inhibit biofilm formation by S. aureus strain SH1000 using a 96-well microtiter plate crystal violet binding assay. When S. aureus cultures were supplemented with PAM extract at a concentration of 10% (by vol), nearly complete inhibition of biofilm formation was observed (FIG. 1A). PAM extract inhibited S. aureus biofilm formation in a dose dependent manner (FIG. 1B). Greater than 50% reduction in crystal violet binding was observed at concentration as low as 0.03%. PAM extract did not inhibit the growth of S. aureus strain SH1000 (FIG. 1C), or of S. aureus Xen29, E. coli JM109 or K. pneumoniae 1840. Colony biofilm extracts prepared from three other K. kingae clinical strains (PYKK081, PYKK129, and PYP8) also exhibited biofilm inhibition activity against S. aureus (FIG. 1D). Biofilm inhibition activity could also be detected in the supernatant of K. kingae PYKK181 broth cultures, but the activity was much weaker than the activity in colony biofilm extracts.

Example 3

K. Kingae PAM Extract Exhibits Surfactant-Like Activity

To determine whether PAM extract can modify the surface properties of an abiotic substrate, evaporation coating was used to deposit PAM extract onto the surface of polystyrene wells, and then the ability of the coated surfaces to resist biofilm formation by *S. epidermidis* and *A. actinomycetemcomitans* was tested (FIG. 2). When PAM extract was coated onto polystyrene surfaces, the coated surfaces efficiently repelled biofilm formation by both species of bacteria (FIG. 2, left panels). When PAM extract was diluted with an equal volume of water, the evaporative coating produced a ring of biofilm inhibition (FIG. 2, middle panels). This ring probably develops as a consequence of surface-tension driven flow resulting from evaporation of liquid at the edge of the drop. The second contact line that develops toward the center of the drop may result from suppression of Marangoni flow due to the presence of organic compounds in the extract, or from capillary forces. When PAM extract was diluted with three volumes of water, the evaporative coating did not efficiently inhibit biofilm formation (FIG. 2, right panels). These findings demonstrate that PAM extract can alter the physiochemical properties of a surface, and suggests that a minimum thickness of coating is necessary for efficient surface modification and biofilm inhibition.

Example 4

*K. Kingae* PAM Extract Interferes with Cell/Substrate Interactions and Disrupts Pre-Formed Biofilms To determine whether PAM extract inhibits binding of *S. aureus* cells to abiotic surfaces, stainless steel or polystyrene rods were placed in tubes containing *S. aureus* single-cell suspensions supplemented with 3% PAM extract, and the numbers of cells attached to the rods after 30 or 60 min (FIGS. 3A and B) were counted. For both materials and both time points, the numbers of cells bound to the rods were significantly less in tubes containing PAM extract than in control tubes ($P<0.05$; Student's t test). PAM extract also significantly inhibited binding of *S. aureus* cells to polycarbonate tubes at concentrations of 0.1 and 1% ($P<0.05$) (FIG. 3C), and significantly detached pre-formed *S. aureus* biofilms at concentrations of 0.1, 0.5 and 1% ($P<0.05$) (FIG. 3D).

Example 5

*K. Kingae* PAM Extract Exhibits Broad-Spectrum Biofilm Inhibition Activity

The ability of PAM extract to inhibit biofilm formation by *K. kingae*, *K. pneumoniae*, *S. epidermidis*, and *C. albicans* in a 96-well microtiter plate assay was measured (FIG. 4). PAM extract inhibited biofilm formation by all four species in a dose-dependent manner.

Example 6

The Biofilm-Inhibiting Activity of *K. Kingae* PAM Extract is Due to Polysaccharide To determine the chemical nature of the biofilm inhibiting compound in PAM extract, PAM extract was treated with DNase I, RNase A and proteinase K. None of these enzymes affected the biofilm-inhibiting activity of the extract. Similarly, extraction of PAM extract with ether, which removes lipids and fatty acids, had no effect on its antibiofilm activity. In contrast, treatment of PAM extract with the carbohydrate active compound sodium metaperiodate, or treatment of the extract with 2M HCl at 100° C. for 2 h, significantly reduced its biofilm inhibiting activity. In addition, the biofilm-inhibiting activity was heat stable (100° C., 15 min) and >100 kDa in size as determined by size exclusion filtration. These findings suggest that the biofilm-inhibiting activity of the PAM extract is a high-molecular-mass polysaccharide.

Example 7

Structural Analysis of *K. Kingae* Exopolysaccharides

NMR analysis of *K. kingae* PAM extract treated with DNase and RNase revealed the presence of galactan (FIG. 5 and Table 1). $^{13}C$ NMR chemical shift patterns and spectra simulations were consistent with the structure →3)-β-D-Galf-(1→6)-β-D-Galf-(1→. This polysaccharide is hereafter referred to as PAM galactan.

TABLE 1

NMR data for *K. kingae* PAM galactan.

| Glycose residue | H/C-1 | H/C-2 | H/C-3 | H/C-4 | H/C-5 | H/C-6 |
|---|---|---|---|---|---|---|
| A | | | | | | |
| →6)-Galf-(1→ | 5.18 | 4.13 | 4.09 | 3.96 | 3.98 | 3.65; 3.88 |
| | 108.10 | 82.40 | 77.80 | 84.40 | 70.70 | 70.30 |
| B | | | | | | |
| →3)-Galf-(1→ | 5.08 | 4.30 | 4.17 | 4.10 | 3.92 | 3.67; 3.73 |
| | 109.40 | 80.40 | 83.80 | 83.20 | 71.90 | 63.90 |

Weaker and broader signals of another polysaccharide (PS2) were also identified (FIG. 5). NOE correlation between H-1 of GlcNAc and H-5 of Kdo, as well as low field shift of C-5 signal of Kdo, indicated that GlcNAc was connected to 0-5 of Kdo in PS2. Low field shift of GlcNAc C-6 (65.5 ppm) were consistent with Kdo linked to this position. Alkaline deacylation of PAM extract with subsequent separation on a Sephadex G-50 column gave a product with decreased molecular mass (PS3). Deamination of this polysaccharide produced OS I. NMR data for OS I allowed us to reliably identify the anomeric configuration of Kdo as β by comparing the position of all $^1H$ and $^{13}C$ NMR signals to published data. These NMR data are consistent with the structure →5)-β-Kdo-(2→6)-α-GlcNAc-(1→ for PS2.

Hydrolysis of PAM extract with acetic acid resulted in a precipitate and a soluble fraction, which contained both PAM galactan and PS2. Additional PS2 could be recovered from the precipitate by 5% NH43380H extraction. Monosaccharide analysis of PAM extract showed the presence of Glc (3% of sample mass), Gal (15%), and GlcN (10%). Kdo was identified after methanolysis and acetylation.

Bradford protein assay using BSA as a standard showed that PAM extract contained approximately 12% protein. A large quantity of non-aromatic peptides was obtained after strong alkaline deacylation of PAM extract. Fatty acid analysis of PAM extract showed C14 and C16 acids, as well as unsaturated C16 and C18. The C14 acids were the main component. A small amount of lipid was also present. A disaccharide (OS2) was obtained after deacylation of the precipitate, indicating the presence of LPS. However no characteristic 3-OH fatty acids for LPS were detected by GC-MS analysis. Together, PAM galactan and PS2 constituted 30-50% of the PAM extract sample. PS2 is identical to a capsular polysaccharide produced by *Actinobacillus pleuropneumoniae* serotype 5.

Example 8

Purified *K. Kingae* PAM Galactan Exhibits Biofilm Inhibition Activity

PAM extract was fractionated on a Sephadex G-50 column. PAM galactan eluted after the void volume but spread significantly. Pooled PAM fractions yielded a homogeneous high molecular-mass polysaccharide that was free of PS2 as determined by NMR spectroscopy. Purified PAM galactan exhibited biofilm-inhibiting activity against *S. aureus, K. kingae* and *K. pneumoniae* (FIG. 6), demonstrating that PAM galactan is an active biofilm-inhibiting component of PAM extract.

Example 9

Identification of a Putative *K. Kingae* PAM Gene Cluster

In bacteria, the biosynthesis of galactofuranose is catalyzed by the enzyme UDP-galactopyranose mutase, which converts UDP galactopyranose to UDP-galactofuranose. A search of the whole genome shotgun sequence assembly of *K. kingae strain PYKK*081 was performed for homologues of *E. coli* ugm, which encodes UDP-galactopyranose mutase. An open reading frame that encodes a protein exhibiting 64% amino acid identity to *E. coli* UDP378 galactopyranose mutase was identified. The *K. kingae* ugm homologue was located in a cluster of five genes designated pamABCDE, where pamB encodes the UDP-galactopyranose mutase, and pamA, pamC, pamD and pamE encode putative glycosyltransferases. The G+C content of pamABCDE is less than that of the flanking regions, suggesting that these genes may have been acquired by horizontal transfer. Among the flanking genes, orf2 encodes the β subunit of glycyl-tRNA synthetase, and orf8 encodes a conserved hypothetical protein that is present in the genomes of many Neisseriaceae. It was predicted that the pamABCDE gene cluster is involved in the production of PAM galactan. A genetic map of the *K. kingae* pamABCDE gene cluster and flanking regions is shown in FIG. 7A.

Example 10

Expression of the *K. Kingae* PAM Genes in *E. Coli*

To confirm that the *K. kingae* pamABCDE genes are involved in the production of PAM galactan, orf2pamAB, pamABC, and pamABCDE from *K. kingae* strain PYKK181 were amplified by PCR, the PCR products were cloned into a high-copy-number plasmid downstream from an IPTG-inducible tac promoter, and the plasmids were transformed into *E. coli*. The nucleotide sequence of pamABCDE from *K. kingae* strain PYKK181 was 97% identical to the orthologous sequence from *K. kingae* strain PYKK081. Schematic diagrams of the genes carried on the expression plasmids are shown in FIG. 7B.

Extracts were prepared from colony biofilms of plasmid harboring *E. coli* transformants and tested for their ability to inhibit biofilm formation by *S. aureus* in the microtiter plate assay (FIG. 7C). The biofilm inhibition activity of extracts prepared from the pMB10-harboring transformant (containing orf2pamAB) was not significantly different than that of extracts prepared from the plasmid vector control. In contrast, extracts prepared from pMB5- and pMB9-harboring strains (containing pamABC and pamABCDE, respectively) inhibited *S. aureus* biofilm formation as evidenced by a reduction in the amount of crystal violet binding (FIG. 7C). In addition, NMR spectra revealed anomeric signals corresponding to PAM galactan in colony biofilm extracts prepared from pMB5-harboring *E. coli*, but not from the plasmid vector control. These results demonstrate that the *K. kingae* pamABC genes are sufficient for the production of bioactive PAM galactan in *E. coli*.

Homologues of pamABC are present in the genome of the oral bacterium *Simonsiella mulleri*, and a modified pamABC gene cluster containing one additional gene located between pamA and pamB is present in the genome of the swine respiratory pathogen *Actinobacillus pleuropneumoniae*. Preliminary results indicate that extracts prepared from *S. mulleri* and *A. pleuropneumoniae* colony biofilms also exhibit broad spectrum antibiofilm activity.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and GenBank sequences cited in this disclosure are incorporated by reference in their entireties. The citation of any references herein is not an admission that such references are prior art to the present invention.

The invention claimed is:

1. A composition comprising a linear polysaccharide comprising →3)-β-D-Galf-(1→6)-β-D-Galf-(1→subunits.

2. A pharmaceutical composition comprising the composition of claim 1 and a pharmaceutically acceptable carrier.

3. The pharmaceutical composition of claim 2, wherein said pharmaceutical composition is in oral administration form.

4. The pharmaceutical composition of claim 3, wherein said pharmaceutical composition is a lozenge, a mouth wash, or a piece of chewing gum.

5. The pharmaceutical composition of claim 2, wherein said composition is in topical administration form.

6. The pharmaceutical composition of claim 5, wherein said composition is an ointment, a cream or a lotion.

* * * * *

SEQUENCE LISTING

```
<160> NUMBER OF SEQ ID NOS: 15

<210> SEQ ID NO 1
<211> LENGTH: 800
<212> TYPE: DNA
<213> ORGANISM: Kingella kingae

<400> SEQUENCE: 1
atgttccaat taagcgaaat tccaacagaa atagcggttt ttattgcaac acataaatca      60
tttcagcgac cagaaggtca tgtattcgtg ccattgcaat taggtaatca gccagaaaat     120
ctaggctatt tacgcgaaaa tcaattagat aatatagccg ataaaaaccc ctattttgt     180 gaattaaccg cactatattt cttatggaaa aatgtccata ctcctgtgat aggcttggtg     240
cattaccgta gatattttgc aaaaaagcga aacatagttc aaagaagaat caatcaactc     300
```

```
gcttatttat taggactcgt tccgaagcaa caaacctctc gccataccat actcacttcc    360
gatgagattc agcaactatg gcaaaactct caagcagatt taatcgtccc agctggtgtt    420
gatttagaca cttcgcttta tgataattat aatcaaaatc atcatattca agattggcat    480
atcgtcaaac aaatcgtaga agaaaaagca ccacaatatt ccctcactat tgcaaaagtt    540
gaacaaaatt gcattcttta cccttataat atgtttatcg gtaaaaaaga aataatcaat    600
gattattgcg aatggctatt tgatattttg tttgaagcag aaaagaaaat tgactgttcc    660
caatacgata gctataacca agagttttc ggcttttag cagaacgatt atttaccgca    720
tggattgtac acaatcaaaa taaatacaaa ataaaacatg tgcctgttca gcgggtacaa    780
acataactag gaataaaaac                                               800

<210> SEQ ID NO 2
<211> LENGTH: 1210
<212> TYPE: DNA
<213> ORGANISM: Kingella kingae

<400> SEQUENCE: 2
atgaattttt tatgtgtcgg agcaggtttt tcctgcgctg ttatcgcaag agaattggct     60
caagcagggc ataaagtaac catcattgac caacgcgccc acaccgcagg caactgccac    120
accgaacgcg atgccgaaac aggtgtaatg gttcatatct acggaccaca cattttccac    180
accgataacg aaactgtatg gaattatttg cagcaatttg gcgaatttat gccttatacc    240
aaccgcgtta agcagtaag cggaggtcag gtatattcat taccagttaa tctacacacg    300
attaaccaat tctacggcaa acattctcg ccaaaagaag ccaaagcatg gattaccaag    360
caatctgacc aaaccattgc cgaaccgcaa acttttgaag aacaagccat gaaatttgtt    420
ggcaaagacc tgtatcaagc cttcttcaaa ggttataccg ccaaacaatg gggcgtatcg    480
ccaaccaaat tgcctgctag cattttgaaa cgcttgccag tgcgttttaa ttatgatgac    540
aactattttg ctcacaaatt ccaaggtata cccaaaaatg gctataccga aatcgtggac    600 aatatttga atcacgaaaa cattaccgta aaattgaaca cgccatacag cgaagatatg    660
caatctgaat cgaccatgt tttctggtct gcaccgttgg atttgtggtt caaacaccaa    720
ttcggaaaat taggttatcg cacattggat tttgaaacat tccgcgatga aggcgatttc    780
caaggtaatg ctgtaattaa ctattgcgat gaaactgtgc cgttcacacg cattaccgaa    840
cacaaacact tctcgccttg ggaacagcac gaaaaaacct tgtgctacaa agaatacagc    900
cgaacttgca aagatggcga tattccttac tatccaatcc gattagcaga agaccaagcc    960
ttgttatcgc aatatgaaac tgttgccaac caagcaaaag gcgtaagctt tgtaggacgt   1020
ttaggtactt atcgctactt ggatatggac gtaaccattg cggaagcact taaaacagcg   1080
caaggcgtgt tggcagatat tgccaataag caggaaatta aaccgttta ttttcttaa    1140 ttttcagca tttcaggcag cctgcaaaag gctgtctgaa atatttatca tttcaaaata   1200
ttaaacaatc                                                         1210

<210> SEQ ID NO 3
<211> LENGTH: 1779
<212> TYPE: DNA
<213> ORGANISM: Kingella kingae

<400> SEQUENCE: 3
atgaatatta tccaaaatct cgtttttccca aatctagaca ttcaagcccc cgatgattta     60
tacgttcgtt attggggtgg tacgcaagca ttccgaaatg aaagagaaat ccgtttccta    120
```

-continued

```
caaaaaggag ctggttgcgt ttttgatacc tttttcaact cgtttaccat tcaaacttgg      180
aaaaacaaaa ccaatatccg ccaaattaaa ttgcgtttat tcggtcatgg cgagttttta      240
atcaaaatcc gccgccacaa gttgcacgaa gacatgaaac atttaaatga attaaccatt      300
caattaaatg aatcaggcac ggacattgat ttcgcagatt tgaacgacca cacagaaggc      360
atgctgtttt ttgaattgat ttcattaaca gataatgctt atgtaaaccg tggtttttat      420
cacactgatt tagaaccgca gaatcctgta aaattaggca ttgtgattac acacttcaac      480
cgtaaacatt acgttttacc tgcgattgac cgcgtatcta atgatttgct gcaagaccct      540
tattacaaag ataaaattag tctgattgtt gtagataact cacaaaacat cacacaagaa      600
gaagccaaac acgcgattgt tattccaaat caaaacttgg gtggctctgg tggttttact      660
cgtggtttga tgtatttgga agatgaaaaa agctatacgc actgcttatt tatgggacgat      720 gatgcgtctt gtgaaattga aagcattcgt cgtgcttatg cgctgttgca gtatgcaaca      780
actgagaaat ttgcagtttc tggggcacag ttacgtgaag ctgcaccatc cattttgcat      840
gaaaaatcag cgcaatttac tcaattcggt attcctttgc atcacggtaa aaatatgcaa      900
agcgtttatg attattaac atcagaatta gattgtgata cagcaaatta tgctgcatgg      960
tggttctgtg ctttaaact cacagatgta gaaaagtatg cattcccatt ttttgtacgc     1020
ggtgatgata tttgttttag tttatcaaat aaatttaata tttgctctat gaacggcata     1080
ggtgtttggg ctgaagattt ttttattaaa gaaggtttat ggacacgtta tctaacgttt     1140
agagctgacg cagttttaaa ctccgtattt aatacaaaaa attacaataa atccatactt     1200
aaaaaatggt tctctcattt atattgggga tgtgtatatt catataatta ttcatcagct     1260
gctgcattta aattagcatt agaagatttt ttagcaggaa cacagacttt tgttcatgat     1320
atgacagcca gtcatgctcg tgcaaaacta gcacagctac cacaagatga aaaaatgcag     1380
cctatcaatc gtatagacta cctaaaatta agatacccaa ctcctgttaa aaagagaaaa     1440
cacgaattac gccgtattat tcgtcaatta acattaaatt atttgttgct acctgaacgt     1500
tttatgaaaa aagggattat ttttcaacct aaacatttcg gtgcaaattt gactgatatt     1560
tatcgttata gacaagttta ttacgaacac gaagcaacac gcacaggcta tgtcgcaacg     1620
tttgataggc aacgtttaat tcaggcttat aaagattatt ttgctgcatt acgtttgatt     1680
gatgaaaaat ttgatacagc aaaagcagat tatttaagta aaaaagatga attaacttct     1740
cgtgctttct gggaaaaaat ttataacact gaaaaataa                           1779
```

<210> SEQ ID NO 4
<211> LENGTH: 1197
<212> TYPE: DNA
<213> ORGANISM: Kingella kingae

<400> SEQUENCE: 4

```
atgaaaattt taatcttaca caaatggcta ataacaggcg gcattgagcg cgtattgatt       60
gattatctgc atattttac tcaacttggg catcaagttg atttatcctt aaaatatgac      120
tttaataatc aatgtgcgct gctggaacaa atcccccagc acatcaaaat agattatttt      180
gccaatgctc aacaaactgc tgcaaaagag tggaaaaagc agcatcgcaa agataattta      240
gccaatagaa tcgcttatga atggcaacgc attattgagc aaaaaaacta tcgcgattat      300
ttggcttcgc gtgttgtcaa ttacaattta gtcattgatt ttagtgattg tttggacgat      360
ataatgcgta tgccaaaatt cttgcaaccg cattttccac caactttgcg ttgggtacat      420
```

| | |
|---|---|
| ttggctttat ccaaggaacc cattttgtca aataaacaaa agcgacgatt tactgctatt | 480 |
| ttttctcagc atacgggtgt tgttgcgatt tgcgatgcga tgcgtcagca aattcaagaa | 540 |
| aatattgact tgcctgaaca taaattgttt tgtttgcaca atccgattgc gctggacaac | 600 |
| attcaaaaac aagcagcgtt gcctgtttca aacacgcatc aagcgttgtt gcaacaacct | 660 |
| ttccttttc aagctgcaag acttgaatct gttaaaaact tgtttgaatt aattgatatt | 720 |
| tatgctgcat taaaaagcaa tcattctatt cagcacaaac tgtacattgc aggcgacggt | 780 |
| agtttgaaaa atgaattgca acataaaatt gatagcttaa atttaagcca agattgcttg | 840 |
| cttttaggca atttagataa tccttatcct tttttaaag cggcaacttt attttttgcac | 900 |
| acttccacgc gcgaaggttt gccaacggtt ttgctggaaa gtatggcttg tggaacgcct | 960 |
| gttgtggcaa tgaattgtcc aactggcgtg gcagatatat tgggtaaaca aagcgagtat | 1020 |
| ggcaaattga ttcctatgca caatcagcaa atgtttcaag aaacagttat ctctttatta | 1080 |
| aatgatgccg aacagcttgc tcaatatcaa caaaaagcaa cgcaacgtgc agcagatttt | 1140 |
| agcgcagagc aaatcagcca aaatgtgcag tctattttag aaatgcttaa accatga | 1197 |

<210> SEQ ID NO 5
<211> LENGTH: 792
<212> TYPE: DNA
<213> ORGANISM: Kingella kingae

<400> SEQUENCE: 5

| | |
|---|---|
| atgatttcta cctatatcat ctccctagcc agcgaaaccc aacgccgagc gcacatgaaa | 60 |
| gcgcaagccg agcgttatca actcaatgcc gcatttttg atgcggtgga tatgcgccaa | 120 |
| gccacgcaaa cggatattga acatttaagc gttctgccaa acataaaaa gcccaaaaaa | 180 |
| cagcgttggt taagcaaggg cgagctgggg tgtgctttga gtcatcatca aatttatcaa | 240 |
| gaaatgataa ataaacagct agattatgcg tttatttgg aagacgatgc ccgttttttg | 300 |
| caatcaccaa aagctttgtt gttgcccgaa aatctacgca aaattgctgc tcaatatgat | 360 |
| tttgatattt tgattttggg ttatgtaaaa acgctggaac atcaattgcc gtattatcat | 420 |
| cgccgtattc caattaaaaa acgtgcaaca ttgcaactgc cgaacaaac gattcaattt | 480 |
| ggcacgcctt gggaacaata tggctgtggc gcagtggctt atgtgattac taaaaaaggc | 540 |
| gcggaaaagc tgctcaacat cacgcaaaaa ccatgcgtcc cagccgatga ttggctatat | 600 |
| tttgagcaac attgcggtgt aaaagtgctg cacgctcgcc ctactttgt gctggaagat | 660 |
| ttggaacagt tggtcagcac cattcgggta gaaaaagcca attttttgca acccaagttg | 720 |
| tccagcatta tcattcgcag catcaaaggc tggtgtaaac acatcgccat gaattatttg | 780 |
| ggatttaaat aa | 792 |

<210> SEQ ID NO 6
<211> LENGTH: 800
<212> TYPE: DNA
<213> ORGANISM: Kingella kingae

<400> SEQUENCE: 6

| | |
|---|---|
| atgttccaat taagcgaaat tccaacagaa atagcggttt ttattgcaac acataaatca | 60 |
| tttcagcgac cagaaggtca tgtattcgtg ccattgcaat taggtaatca gccagaaaat | 120 |
| ctaggctatt tacgcgaaaa tcaattagat aatatagccg ataaaaaccc ctattttgt | 180 |
| gaattaaccg cactatattt cttatggaaa aatgtccata ctcctgtgat aggcttggcg | 240 |
| cattaccgta gatattttgc aaaaaagcga acatagttc aagaagaat caatcaactc | 300 |

```
gcttatttat taggactcgt tccgaagcaa caaacctctc gccataccat actcacttcc      360
gatgagattc agcaactatg gcaaaactct caagcagatt taatcgtccc agctggtgtt      420
gatttagaca cttcgcttta tgataattat aatcaaaatc atcatattca agattggcat      480
atcgtcaaac aaatcgtaga agaaaaagca ccacaatatt ccctcactat tgcaaaagtt      540
gaacaaaatt gcattcttta cccttataat atgtttatcg gtaaaaaaga aataatcaat      600
gattattgcg aatggctatt tgatattttg tttgaagcag aaaagaaaat tgactgttcc      660
caatacgata gctataacca aagagttttc ggcttttag cagaacgatt atttaccgca       720
tggattgtac acaatcaaaa taaatacaaa ataaaacatg tgcctgttca gcgggtacaa      780
acataactag gaataaaaac                                                  800

<210> SEQ ID NO 7
<211> LENGTH: 1210
<212> TYPE: DNA
<213> ORGANISM: Kingella kingae

<400> SEQUENCE: 7
atgaattttt tatgtgtcgg agcaggtttt tcctgcgctg ttatcgcaag agaattggct       60
caagcagggc ataaagtaac catcattgac caacgcgccc acaccgcagg caactgccac      120
accgaacgcg atgccgaaac aggtgtaatg gttcatatct gcggaccaca cattttccac      180
accgataacg aaactgtatg gaattatttg cagcaatttg gcgaatttat gccttatacc      240
aaccgcgtta agcagtaag cggaggtcag gtatattcat taccagttaa tctacacacg       300
attaaccaat tctacggcaa aacattctcg ccaaaagaag ccaaagcatg gattaccaag      360
caatctgacc aaaccattgc cgaaccgcaa acttttgaag aacaagccat gaaatttgtt      420
ggcaaagacc tgtatcaagc cttcttcaaa ggttgtaccg ccaaacaatg ggcgtatcg       480 ccaaccaaat tgcctgctag cattttgaaa cgcttgccag tgcgttttaa ttatgatgac      540
aactattttg ctcacaaatt ccaaggtata cccaaaaatg gctataccga atcgtggac       600 aatattttga atcacgaaaa cattaccgta aaattgaaca cgccatacag cgaagatatg      660
caatctgaat acgaccatgt tttctggtct gcaccgttgg atttctggtt caaacaccaa      720
ttcggaaaat taggttatcg cacattggat tttgaaacat tccgcgatga aggcgatttc      780
caaggtaatg ctgtaattaa ctattgcgat gaaactgtgc cgttcacacg cattaccgaa      840
cacaaacact tctcgccttg ggaacagcac gaaaaaacct tgtgctacaa agaatacagc      900
cggacttgcg aagatggcga tattccttac tacccaatcc gattagcaga agaccaagcc      960
ttgttatcgc aatatgaaac tgttgccaac caagcaaaag gcgtaagctt tgtaggacgt     1020
ttaggtactt atcgctactt ggatatggac gtaaccattg cggaagcact taaaacagcg     1080
caaggcgtgt tggcagatac tgccaataag caggaaatta aaccgttta ttttttcttaa    1140 tttttcagca tttcaggcag cctgcgaaag gctgtctgag atatttatca tttcaaaata    1200
ttaaacaatc                                                            1210

<210> SEQ ID NO 8
<211> LENGTH: 1779
<212> TYPE: DNA
<213> ORGANISM: Kingella kingae

<400> SEQUENCE: 8
atgaatatta cccaaaatct cgttttccca aatctagaca ttcaagcccc cgatgattta       60
```

-continued

```
tacgttcgtt attggggtgg tacgcaagca ttccgaaatg aaagagaaat ccgtttccta        120
caaaaaggag ctggttgcgt ttttgatacc tttttcaact cgtttaccat tcaaacttgg        180
aaaaaccaaa ccaatatcca ccaaattaaa ttgcgtttat tcggtcatgg cgagttttta        240
atcaaaatcc gccgccacaa gttgcacgaa gacatgaaac atttaaatga attaaccatt        300
caattaaatg aatcaggcac ggacattgat ttcgcagatt tgaacgacca cacagaaggc        360
atgctgtttt ttgaattgat ttcattaaca gataatgctt atgtaaaccg tggtttctat        420
cacactgatt tagaaccgca gaatcctgta aaattaggca ttgtgattac gcacctcaac        480
cgtaaacatt gcgttttacc tgcgattgac cgcgtatcta atgatttgct gcaagaccct        540
tattacaaag ataaaattag tctgattgtt gtagataact cacgaaacat cacacaagaa        600
gaagccaaac acgcgattgt tattccaaat caaaacttgg gtggctctgg tggttttact        660
cgtggtttga tgtatttgga ggatgaaaaa agctatacgc actgcttatt tatggacgat        720
gatgcgtctt gtgaaattga aagcattcgt cgtgcttatg cgctgttgca gtatgcaaca        780
actgagaaat ttgccgtagc aggggctcaa ttacaagaat cagaaccgta taaaattcat        840 gaaaaggag ctgtgttttc tagattatct tatcaatcta tctgccatgg tttagataca        900
cgtaatgctc atgatgtttt attggctgag attagtgatg ttaaacctaa ttatggtggt        960
tggtggttat ttgcctttaa gataaaagat attaagtttt actcatttcc tttctttgtt       1020
cgcggtgatg atgttttcatt cggctttatg aacgaattta atattacaac tctaaatggg       1080
attaatgttt gggcggaaga ttttttttatt aaagagggat tatggacacg ttatctggga       1140
tttagagggt catgtgtttc tacaattta caagattcag attatagtaa atccaaaatt       1200
cgtaaagtat ttaaacaatg gtatttttaat tgcattcatt cttataatta ttcttcagct       1260
aaagcaatta ttttagcttt agaagacttt ttagcaggaa cacaagcatt tacaagcgat       1320
atgacagcaa gcaatgctcg tgcaaaacta gcacagctac cacaagatga aaaaatgcag       1380
cctatcaatc gcatagacta ccctaaatta agatacccaa ctcctgttaa aaagagaaaa       1440
cacgaattac gccgtattat tcgtcaatta acattaaatt atttgttgct acctgaacgt       1500
tttatgaaaa aagggattat ttttcaacct aaacatttcg gtgcaaattt gactgatatt       1560
tatcgttatg acaagtttta ttacgaacac gaagcaacac gcacaggcta tgtcgcaacg       1620
tttgataggc aacgtttaat tcaggcttat aaagattatt ttgctgcatt acgttttgatt       1680 gatgaaaaat ttgatacagc aaaagcagat tatttaagta aaaaagatga attaacttct       1740
cgtgctttct gggaaaaaat ttataacact gaaaaataa                              1779
```

<210> SEQ ID NO 9
<211> LENGTH: 1197
<212> TYPE: DNA
<213> ORGANISM: Kingella kingae

<400> SEQUENCE: 9

```
atgaaaattt taatcttaca caaatggcta ataacaggcg gcattgagcg cgtattgatt         60
gattatccgc atattttac tcaacttggg catcaagttg atttatcctt aaaatatgac        120
tttaataatc aatgtgcgct gctggaacaa atcccccagc acatcaaaat agattatttt        180
gccaatgctc aacaaactgc tgcaaaagag tggaaaaagc agcatcgcaa agataattta        240
gccaatagaa tcgcctatga atggcaacgc attattgagc aaaaaaacta tcgcgattat        300
ttggcttcgc gtgttgtcaa ttacaattta gtcattgatt ttagtgattg tttggacgat        360
ataatgcgta tgccaaaatt cttgcaaccg cattttccac caactttgcg ttgggtacat        420
```

-continued

```
ttggctttat ccaaggaacc cattttgtca aataaacaaa agcgacgatt tactgctatt    480
ttttctcagc attcgggtgt tgttgcgatt tgcgatgtga tgcgtcagca aattcaagaa    540
aatattgact tgcctgaaca taaattgttt tgtttgcaca atccgattgc gctggacaac    600
attcagaaac aagcagcgtt gcctgtttca aacacgcatc aagcgttgtt gcaacaacct    660
ttcctttttc aagctgcgag acttgaatct gttaaaaact tgtttgaatt aattgatatt    720
tatgctgcat taaaaagcaa tcattctatt cagcacaaac tgtacattgc aggcgacggt    780
agtttgaaaa atgaattgca acataaaatt gatagcttaa atttaagcca agattgcttg    840
cttttaggca atttagataa tccttatcct ttttttaaag cggcaacttt attttttgcac    900
acttccacgc gcgaaggttt gccaacggtt ttgctggaaa gtatggcttg tggaacgcct    960
gttgtggcaa tgaattgtcc aactggcgtg gcagatatat gggtaaaca aagcgagtat   1020
ggcaaattga ttcctatgca caatcagcaa atgtttcaag aaacagttat ctctttatta   1080
aatgatgccg aacagcttgc tcaatatcaa caaaaagcaa cgcaacgtgc agcagatttt   1140
agcgcagagc aaatcagcca aatgtgcag tctattttag gaatgcttaa accatga      1197
```

<210> SEQ ID NO 10
<211> LENGTH: 792
<212> TYPE: DNA
<213> ORGANISM: Kingella kingae

<400> SEQUENCE: 10

```
atgatttcta cctatatcat ctccctagcc agcgaaaccc aacgccgagc gcacatgaaa     60
gcgcaagccg agcgttatca actcaatgcc gcattttttg atgcggtgga tatgcgccaa    120
gccacgcaaa cggatattga acatttaagc gttctgccaa acataaaaa gcccaaaaaa    180
cagcgttggt taagcaaggg cgagctgggg tgtgctttga gtcatcatca aatttatcaa    240
gaaatgataa ataaacagct agattatgcg tttattttgg aagacgatgc ccgtttttg    300
caatcgccaa aagatttgtt gttacccgaa aatctacgcg aaattgctgc tcaatatgat    360
tttgatattt tgattttggg ttatgtaaaa acgctggaac atcaattgcc gtattatcat    420
cgccgtattc caattaaaaa acgtgcaaca ttgcaactac ccgagcaaac gattcaattt    480
ggcacgcctt gggaacaata tggctgtggc gcggtggctt atgtgattac taaaaaaggc    540
ccgggaaagc tgctcaacat ctcgcaaaaa ccatgcgtcc cagccgatga ttggctatat    600
tttgagcaac tttgcagtgt aaaagtgcgg cacgctcccc ctactttgt gctggaacat    660
ttagaacagt tggtcatcac cattcgggta gaaaaagcca attctttgca acccatgttg    720
tccgctttta tcattcgcag catcaaaggc tggtgtaaac acatcaccat gaattatttg    780
ggatttaaat aa                                                       792
```

<210> SEQ ID NO 11
<211> LENGTH: 18
<212> TYPE: DNA
<213> ORGANISM: Artificial
<220> FEATURE:
<223> OTHER INFORMATION: Synthetic primer

<400> SEQUENCE: 11

```
tggtaggcaa agtttgcg                                                  18
```

<210> SEQ ID NO 12
<211> LENGTH: 18
<212> TYPE: DNA

```
<213> ORGANISM: Artificial
<220> FEATURE:
<223> OTHER INFORMATION: Synthetic primer

<400> SEQUENCE: 12
ttgatgaatg cagtggcg                                                 18

<210> SEQ ID NO 13
<211> LENGTH: 19
<212> TYPE: DNA
<213> ORGANISM: Artificial
<220> FEATURE:
<223> OTHER INFORMATION: Synthetic primer

<400> SEQUENCE: 13
atgccgcctg ttattagcc                                                19

<210> SEQ ID NO 14
<211> LENGTH: 18
<212> TYPE: DNA
<213> ORGANISM: Artificial
<220> FEATURE:
<223> OTHER INFORMATION: Synthetic primer

<400> SEQUENCE: 14
tgccttcggt gtgaaagg                                                 18

<210> SEQ ID NO 15
<211> LENGTH: 18
<212> TYPE: DNA
<213> ORGANISM: Artificial
<220> FEATURE:
<223> OTHER INFORMATION: Synthetic primer

<400> SEQUENCE: 15
cgtaccaccc caataacg                                                 18
```